(12) United States Patent
Ennist et al.

(10) Patent No.: US 11,139,051 B2
(45) Date of Patent: Oct. 5, 2021

(54) SYSTEMS AND METHODS FOR DESIGNING CLINICAL TRIALS

(71) Applicant: Origent Data Sciences, Inc., Vienna, VA (US)

(72) Inventors: David L. Ennist, Bethesda, MD (US); Albert A. Taylor, Tacoma, WA (US); Danielle E. Beaulieu, Washington, DC (US); Michael A. Keymer, Arlington, VA (US)

(73) Assignee: Origent Data Sciences, Inc., Vienna, VA (US)

( * ) Notice: Subject to any disclaimer, the term of this patent is extended or adjusted under 35 U.S.C. 154(b) by 150 days.

(21) Appl. No.: 16/149,954

(22) Filed: Oct. 2, 2018

(65) Prior Publication Data
US 2020/0105380 A1  Apr. 2, 2020

(51) Int. Cl.
*G16H 10/20* (2018.01)
*G16H 10/60* (2018.01)
*G16H 50/30* (2018.01)

(52) U.S. Cl.
CPC .............. *G16H 10/20* (2018.01); *G16H 10/60* (2018.01); *G16H 50/30* (2018.01)

(58) Field of Classification Search
CPC ......... G16H 10/20; G16H 10/60; G16H 50/30
(Continued)

(56) References Cited

U.S. PATENT DOCUMENTS 7,752,057 B2   7/2010   Ikeguchi et al.
7,853,626 B2   12/2010  Jung et al.
(Continued)

FOREIGN PATENT DOCUMENTS

JP    2013122790    6/2013
WO   WO-2005091203 A2 *  9/2005  .......... G06T 7/0012
(Continued)

OTHER PUBLICATIONS

International Search Report and Written Opinion dated Jan. 31, 2020, directed to International Application No. PCT/US2019/054147; 17 pages.
Beaulieu, et al. (2018) "Machine Learning Tools for Improving the Efficiency of Drug Development Clinical Trials in ALS," Origent Data Sciences, Inc., Vienna, Virginia; 1 page.
Cook, et al. (2004) "Subgroup Analysis in Clinical Trials," The Medical Journal of Australia (MJA) 180: 289-291.
(Continued)

*Primary Examiner* — Hiep V Nguyen
(74) *Attorney, Agent, or Firm* — Morrison & Foerster LLP

(57) ABSTRACT

A method for enrolling patient candidates in a clinical trial includes generating first prediction data indicating predicted progression of a condition for a first group of patients that participated in a first clinical trial using a predictive model and clinical data associated with the first group of patients; grouping clinical trial data into subsets based on the first prediction data; analyzing each subset of clinical trial data to generate a measure of efficacy of the treatment; establishing screening criteria for a second clinical trial by identifying at least one subset that has a measure of efficacy that is higher than a measure of efficacy of the treatment for the full first group of patients; receiving clinical data of a candidate for the second clinical trial; generating second prediction data for the candidate; and enrolling the candidate in the second clinical trial when the second prediction data satisfies the screening criteria.

55 Claims, 12 Drawing Sheets
(9 of 12 Drawing Sheet(s) Filed in Color)

(58) Field of Classification Search
USPC .............................................................. 705/3
See application file for complete search history.

(56) References Cited

U.S. PATENT DOCUMENTS

| | | | |
|---|---|---|---|
| 9,311,276 | B2 | 4/2016 | Jin et al. |
| 2007/0294113 | A1 | 12/2007 | Settimi |
| 2008/0082582 | A1 | 4/2008 | Jung et al. |
| 2009/0131758 | A1* | 5/2009 | Heywood ............ A61B 5/4824 600/300 |
| 2010/0312073 | A1 | 12/2010 | Yarnitsky |
| 2017/0169180 | A1 | 6/2017 | Hamann et al. |

FOREIGN PATENT DOCUMENTS

| | | | |
|---|---|---|---|
| WO | 2009114591 A1 | 9/2009 | |
| WO | 2016/133708 | 8/2016 | |
| WO | WO-2016133708 A1 * | 8/2016 | ............ G16B 50/00 |

OTHER PUBLICATIONS

Goyal, et al. (2014) "Clinical and Molecular Markers That Predict Severity of Relapsing-Remitting MS (RRMS) Disease Dutcomes," Multiple Sclerosis Journal 20: 400-401.

Guideline on the Investigation of Subgroups in Confirmatory Clinical Trials (Jan. 23, 2014), European Medicines Agency, Committee for Medicinal Products for Human Use; 20 pages.

* cited by examiner

| Regression Models | | Time-to-Event Models | |
|---|---|---|---|
| 1 | ALSFRS-R total score | 7 | % Expected VC |
| 2 | Bulbar function | 8 | Loss of speech (Q1 ≤ 1) |
| 3 | Fine motor function | 9 | Wheelchair use (Q8 ≤ 1) |
| 4 | Gross motor function | 10 | Feeding tube (Q5A to 5B) |
| 5 | Respiratory function | 11 | 50% Expected VC |
| 6 | Vital Capacity | 12 | Survival |

FIG. 2

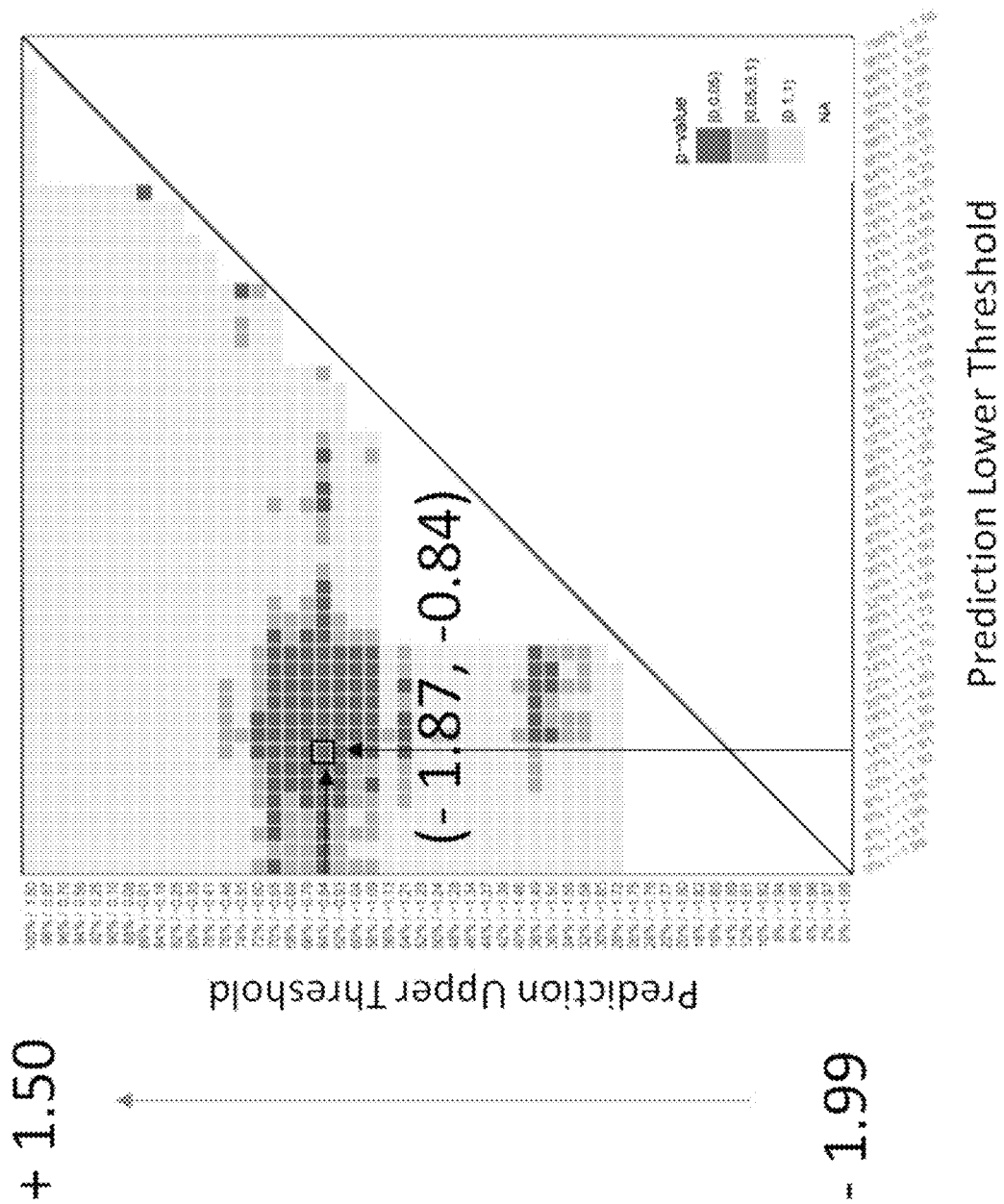

SYSTEMS AND METHODS FOR DESIGNING CLINICAL TRIALS

FIELD OF THE INVENTION

This application generally relates to designing and conducting human clinical trials.

BACKGROUND OF THE INVENTION

Human clinical trials for diseases that have high heterogeneity of disease progression are extraordinarily difficult. Examples of such diseases include Amyotrophic Lateral Sclerosis (ALS), Alzheimer's disease, Huntington's disease, Parkinson's disease, cancers, many chronic medical conditions (such as diabetes, hepatitis C, and others), and mental health conditions such as depression and PTSD. ALS provides a classic illustrative case: two of the most famous ALS patients are Lou Gehrig and Stephen Hawking. Gehrig died within about two years of his diagnosis, while Hawking lived with ALS for over five decades. Hawking's longevity is not due to some sort of superior ALS treatment—this is simply the way that the disease manifests. Some patients reach mortality and progress through the disease quickly, others progress very gradually over decades, and many others will progress at varying rates, alternating among fast, average, slow over time.

This disease progression heterogeneity creates extraordinary challenges for drug discovery and drug development companies who are trying to conduct human clinical trials. For example, a human clinical trial may unknowingly enroll patients with a wide range of disease progression, including many slow (like Hawking) and fast (like Gehrig) progressing patients. Such a trial may be expected to have a lot of variance or "noise" such that a small positive signal among the treated patients cannot be detected above the noise. Thus, the conclusion may be reached that the drug does not work, or does not work well enough, when, in fact, the opposite is true. This false negative may cause the drug development program to be scrapped, resulting in the loss of tens or hundreds of millions of dollars already invested. More significantly, a drug with potential to alleviate human suffering would be abandoned.

SUMMARY OF THE INVENTION

According to some embodiments, methods and systems screen candidates for enrollment in a clinical trial based on data from a previously conducted clinical trial. A predictive model is used to generate disease progression predictions for the patients in the previous clinical trial. A subgroup of the patients that is defined by the disease progression predictions is identified as demonstrating an improved treatment outcome. Candidates for enrollment in the clinical trial are screened by using the predictive model to generate the disease progression predictions for the candidates and comparing the candidates' predictions to the predictions for the subgroup of patients. Candidates can be enrolled or denied enrollment based on the screening or can be selected for various clinical trial subgroups.

According to some embodiments, a method for enrolling patient candidates in a clinical trial for a treatment includes generating first prediction data indicating predicted progression of a condition for a first group of patients that participated in a first clinical trial using a predictive model and clinical data associated with the first group of patients, wherein the predictive model was built based on clinical data associated with a second group of patients having the condition; grouping clinical trial data associated with the first group of patients into a plurality of subsets of clinical trial data based on the first prediction data, wherein each subset of clinical trial data is associated with a corresponding subgroup of the first group of patients; analyzing each subset of clinical trial data to generate a measure of efficacy of the treatment for a subgroup of patients corresponding to the respective subset; establishing at least one screening criteria for a second clinical trial for the treatment by identifying at least one subset of the plurality of subsets that has a measure of efficacy that is higher than a measure of efficacy of the treatment for the full first group of patients, wherein the at least one screening criteria is based on a range of prediction data values that is associated with the identified subset; receiving clinical data associated with a candidate for the second clinical trial for the treatment; generating second prediction data indicating a predicted progression of the condition for the candidate using the predictive model and the clinical data associated with the candidate; determining whether the second prediction data meets the at least one screening criteria; in accordance with a determination that the second prediction data satisfies the at least one screening criteria, enrolling the candidate in the second clinical trial; and in accordance with a determination that the second prediction data fails to satisfy the at least one screening criteria, rejecting the candidate for the second clinical trial.

In any of these embodiments, the method may include selecting the predictive model from a plurality of different predictive models based on a goal for the treatment.

In any of these embodiments, the method may include building the predictive model by training a learning machine on the clinical data for the second group of patients. In any of these embodiments, the method may include standardizing the clinical data for the second group of patients prior to training the learning machine.

In any of these embodiments, the predictive model may predict at least one condition progress metric and the clinical data for the second group of patients comprises data for the at least one condition progress metric.

In any of these embodiments, the clinical data associated with the first group of patients may be clinical data generated prior to the first trial.

In any of these embodiments, a number of patients associated with one subset may be equal to a number of patients associated with at least one other subset.

In any of these embodiments, a number of patients associated with one subset may be different than a number of patients associated with at least one other subset.

In any of these embodiments, the predictive model may predict at least one condition progress metric and the measure of efficacy of the treatment is based on the at least one condition progress metric.

In any of these embodiments, a measure of efficacy of the treatment for the full first group of patients may indicate no statistically significant difference in treatment outcome between a control group and a treatment group.

In any of these embodiments, the measure of efficacy may be generated by comparing treatment outcomes for control patients to treatment outcomes for treated patients.

In any of these embodiments, identifying a subset of the plurality of subsets may include identifying a subset that has a measure of efficacy that meets a threshold test. In any of these embodiments, the threshold test may be a p-value that is no greater than 0.05.

In any of these embodiments, identifying at least one subset of the plurality of subsets may include plotting a representation of the measure of efficacy as a function of subgroup size and prediction data values. In any of these embodiments, plotting the representation of the measure of efficacy may include generating a heat map, wherein a variation in appearance indicates a variation in the measure of efficacy. In any of these embodiments, the heat map may include a representation of the measure of efficacy of the treatment for the full group of patients. In any of these embodiments, identifying at least one subset of the plurality of subsets may include identifying a location on the heat map that is surrounded by locations having the same appearance.

In any of these embodiments, the at least one screening criteria may include a maximum value of the range of prediction data values and a minimum value of the range of prediction data values.

In any of these embodiments, the clinical data for the candidate may be received from a clinician via a clinical trial candidate portal. In any of these embodiments, the method may include sending an instruction to the clinician to enroll or reject the candidate for the second clinical trial.

In any of these embodiments, the range of prediction data values may include an upper threshold prediction data value and a lower threshold prediction data value.

In any of these embodiments, the first prediction data may include predicted patient regression or predicted time to an event.

In any of these embodiments, the patients may be human and the condition may be a disease. In any of these embodiments, the disease may be a neurodegenerative disease or a cancer.

In any of these embodiments, the first clinical trial may be configured to determine at least one of an efficacy of a drug, an efficacy of a different dosage of a drug, or an efficacy of a different combination of drugs.

In any of these embodiments, the method may further include treating the enrolled candidate with the treatment.

According to some embodiments, a system for enrolling candidates in a clinical trial for a treatment, the system comprising one or more processors, memory, and one or more programs stored in the memory and executable by the one or more processors for: generating first prediction data indicating predicted progression of a condition for a first group of patients that participated in a first clinical trial using a predictive model and clinical data associated with the first group of patients, wherein the predictive model was built based on clinical data associated with a second group of patients having the condition; grouping clinical trial data associated with the first group of patients into a plurality of subsets of clinical trial data based on the first prediction data, wherein each subset of clinical trial data is associated with a corresponding subgroup of the first group of patients; analyzing each subset of clinical trial data to generate a measure of efficacy of the treatment for a subgroup of patients corresponding to the respective subset; establishing at least one screening criteria for a second clinical trial for the treatment by identifying at least one subset of the plurality of subsets that has a measure of efficacy that is higher than a measure of efficacy of the treatment for the full first group of patients, wherein the at least one screening criteria is based on a range of prediction data values that is associated with the identified subset; receiving clinical data associated with a candidate for the second clinical trial for the treatment; generating second prediction data indicating a predicted progression of the condition for the candidate using the predictive model and the clinical data associated with the candidate; determining whether the second prediction data meets the at least one screening criteria; in accordance with a determination that the second prediction data satisfies the at least one screening criteria, sending a notification for enrolling the candidate in the second clinical trial; and in accordance with a determination that the second prediction data fails to satisfy the at least one screening criteria, sending a notification for rejecting the candidate for the second clinical trial.

In any of these embodiments, the one or more programs stored in the memory may be executable by the one or more processors for selecting the predictive model from a plurality of different predictive models based on a goal for the treatment.

In any of these embodiments, the one or more programs stored in the memory may be executable by the one or more processors for building the predictive model by training a learning machine on the clinical data for the second group of patients. In any of these embodiments, the one or more programs stored in the memory may be executable by the one or more processors for standardizing the clinical data for the second group of patients prior to training the learning machine.

In any of these embodiments, the predictive model may predict at least one condition progress metric and the clinical data for the second group of patients comprises data for the at least one condition progress metric.

In any of these embodiments, the clinical data associated with the first group of patients may be clinical data generated prior to the first trial.

In any of these embodiments, a number of patients associated with one subset may be equal to a number of patients associated with at least one other subset.

In any of these embodiments, a number of patients associated with one subset may be different than a number of patients associated with at least one other subset.

In any of these embodiments, the predictive model may predict at least one condition progress metric and the measure of efficacy of the treatment is based on the at least one condition progress metric.

In any of these embodiments, a measure of efficacy of the treatment for the full first group of patients may indicate no statistically significant difference in treatment outcome between a control group and a treatment group.

In any of these embodiments, the measure of efficacy may be generated by comparing treatment outcomes for control patients to treatment outcomes for treated patients.

In any of these embodiments, identifying a subset of the plurality of subsets may include identifying a subset that has a measure of efficacy that meets a threshold test. In any of these embodiments, the threshold test may be a p-value that is no greater than 0.05.

In any of these embodiments, identifying at least one subset of the plurality of subsets may include plotting a representation of the measure of efficacy as a function of subgroup size and prediction data values. In any of these embodiments, plotting the representation of the measure of efficacy may include generating a heat map, wherein a variation in appearance indicates a variation in the measure of efficacy. In any of these embodiments, the heat map may include a representation of the measure of efficacy of the treatment for the full group of patients. In any of these embodiments, identifying at least one subset of the plurality of subsets may include identifying a location on the heat map that is surrounded by locations having the same appearance.

In any of these embodiments, the at least one screening criteria may include a maximum value of the range of prediction data values and a minimum value of the range of prediction data values.

In any of these embodiments, the clinical data for the candidate may be received from a clinician via a clinical trial candidate portal. In any of these embodiments, the one or more programs stored in the memory may be executable by the one or more processors for sending an instruction to the clinician to enroll or reject the candidate for the second clinical trial.

In any of these embodiments, the range of prediction data values may include an upper threshold prediction data value and a lower threshold prediction data value.

In any of these embodiments, the first prediction data may include predicted patient regression or predicted time to an event.

In any of these embodiments, the patients may be human and the condition may be a disease. In any of these embodiments, the disease may be a neurodegenerative disease or a cancer.

In any of these embodiments, the first clinical trial may be configured to determine at least one of an efficacy of a drug, an efficacy of a different dosage of a drug, or an efficacy of a different combination of drugs.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The invention will now be described, by way of example only, with reference to the accompanying drawings, in which:

FIG. 2 is an exemplary list of predictive models for generating disease progression metrics for ALS patients, according to some embodiments;

FIGS. 4A and 4B are plots for identifying patient subgroups associated with improved treatment effects, according to another embodiment;

DETAILED DESCRIPTION OF EXEMPLARY EMBODIMENTS

Figure 1A:
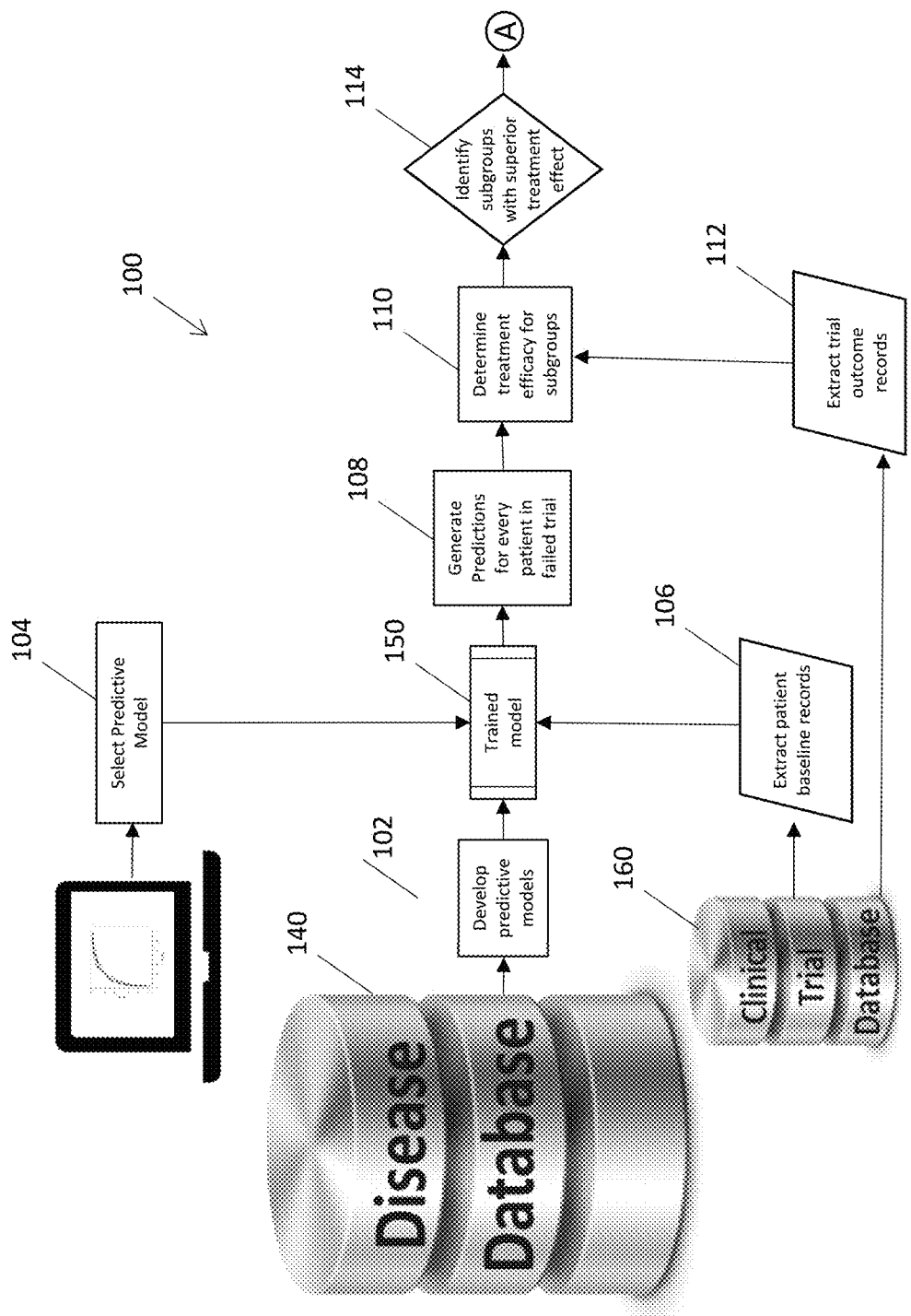
FIGS. 1A and 1B are flow diagrams for a method for enrolling candidates in a clinical trial based on patient-level predictions, according to some embodiments.

Described below are systems and methods for using patient-level predictive algorithms to rescue or improve upon a treatment program in which a clinical trial was previously conducted. According to some embodiments, the systems and methods utilize databases of historical clinical data collected from individual patients having a disease, or other condition, to build a predictive model that can be used to predict the future disease progression for other patients. The predictive model is used to predict the disease progression for the patients that participated in the previously conducted clinical trial using clinical data for the patients that was available prior to administration of the treatment or placebo. Subgroups of the patients are defined based on their predictions. For each subgroup, trial outcome data for the observed treatment arm is compared to trial outcome data for the observed control arm to determine whether there is an observable treatment effect for the subgroup. In other words, subgroups are defined and analyzed to determine whether there is a subgroup of patients, defined by predicted disease progression, where a treatment effect is detectable (i.e., statistically significant). In some embodiments, subgroups are defined and analyzed to identify subgroups in which the combination of treatment effect and variance results in a statistically significant effect size.

Prediction data for the identified subgroup or subgroups is used to screen candidates for a new clinical trial. Patients are screened at the beginning of a clinical trial to predict, for example, a death risk score for each candidate patient, and allowing only those patients whose risk scores fall within the predetermined range to participate in the clinical trial. In another variation, all patients might be included in the trial, but only those meeting the predefined prediction criteria are included in the primary analysis of the trial.

According to some embodiments, the previously conducted clinical trial is a "failed" clinical trial in the sense that the treatment effect was not detectable or strong enough to justify continuing with the treatment development program. However, the previously conducted clinical trial need not be a failed clinical trial. A trial that was not intended to be a registration trial could be the basis for identifying subgroups for analysis in a pivotal trial. For example, an "all comers" trial may be used to identify a subgroup that demonstrated a significant response to a treatment, and the results can be used to design a clinical trial around patients with the same characteristics as the identified subgroup. The initial study could be either a trial that had a placebo control or a trial that had no control. For trials with no control, predictions that assume no treatment effect for each participant could be generated and used as a virtual control to locate subgroups of patients to design a future clinical trial around.

For purposes of the present disclosure, the terms "clinical trial" and "patients" broadly refer to any study of subjects via experimentation. In some embodiments, the subjects are humans and the clinical trials are conducted to test the effectiveness of a treatment for a condition afflicting the human subjects (e.g., a disease). However, the subjects may be animals or cells in tissue culture and clinical trials may refer to trials for treatments for the animals or cells or, more broadly, studies of the animals or cells. This includes the evaluation of veterinary studies (e.g. to determine if a medicine is efficacious for dogs), or for testing on animals or cells new therapies intended for use by humans (e.g. mouse models for testing drugs).

The scope of the studies extends beyond pharmaceutical therapies. It can be applied to any interventional activity, including but not limited to use of a medical device, biologic therapies, exercise and physical therapy, and psychological counseling.

In the following description of the disclosure and embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present invention include process steps and instructions described herein in the form of an algorithm. It should be noted that the process steps and instructions of the present invention could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," or the like, refer to the action and processes of a computer system, or similar electronic computing device, that manipulates and transforms data represented as physical (electronic) quantities within the computer system memories or registers or other such information storage, transmission, or display devices.

The present invention also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Figure 1B:
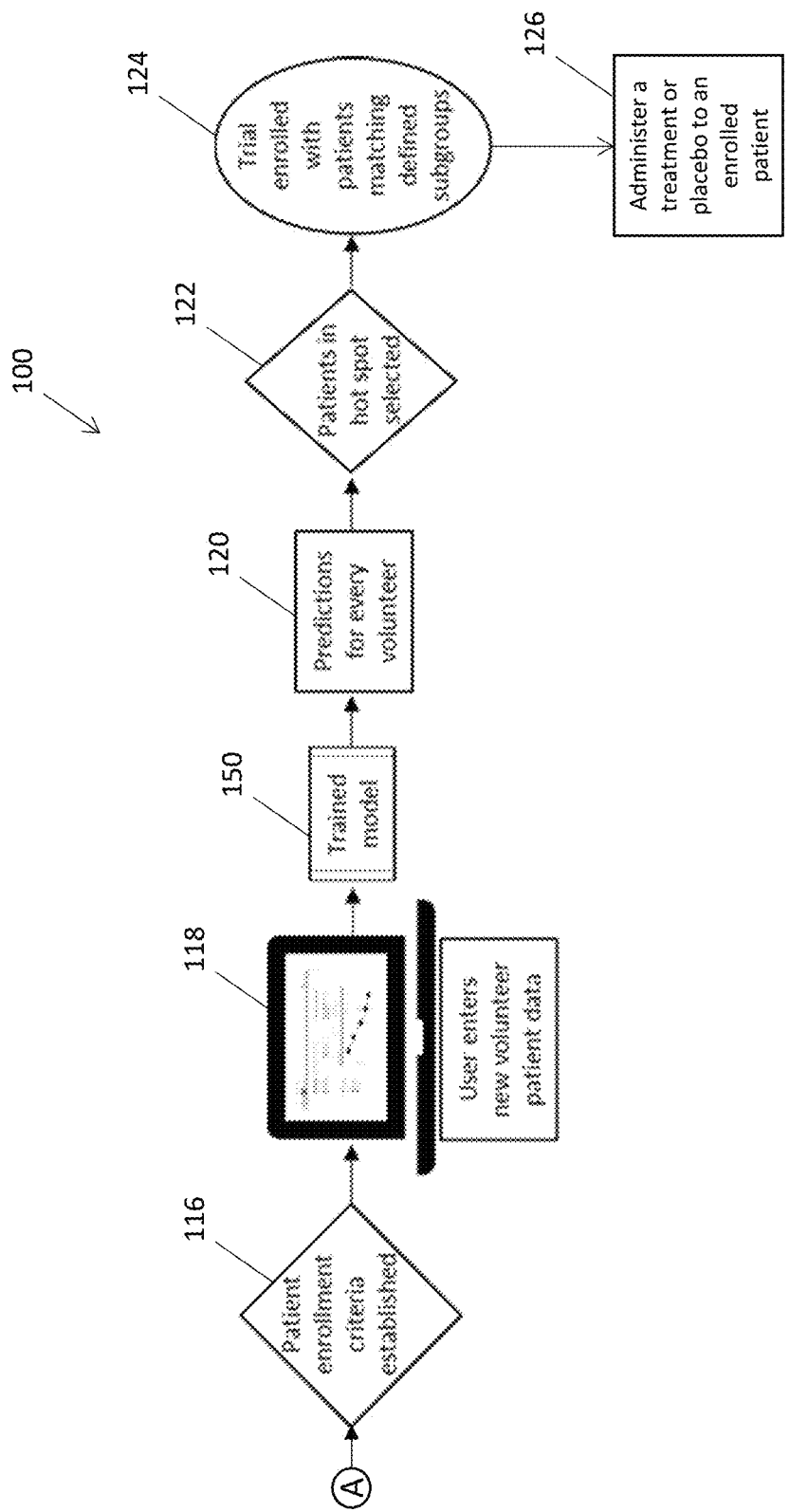

FIG. 1 illustrates a method 100 for enrolling candidates in a new clinical trial based on data from a previous clinical trial. The previous clinical trial and new clinical trial may both be for determining the efficacy of a treatment for a condition, such as a new drug for treatment of a disease. In some embodiments, the previous clinical trial is a failed trial in the sense that there was no statistically significant difference in outcome between a treatment arm and a control (placebo) arm. However, this need not always be the case as discussed further below.

Method 100 identifies one or more subgroups of patients that show an improved outcome relative to the outcome for the full trial population in the previous clinical trial and uses one or more characteristics of the subgroup(s) to screen candidates for the new clinical trial. Candidates having characteristics that match characteristics defining the subgroup(s) generated from the previous clinical trial may be selected to participate in the new trial and/or assigned to specific roles within the new trial.

As noted above, a condition for which method 100 may be used can be a disease, disorder, or any other condition for which an effective treatment is sought. Examples of such diseases are coronary heart disease, cardiovascular disease, stroke, Diabetes mellitus, neurodegenerative conditions including dementia, parkinsonism-dementia (PD) and amyotrophic lateral sclerosis (ALS), liver cirrhosis, musculoskeletal diseases, cutaneous conditions, endocrine conditions, eye diseases, intestinal diseases, infectious diseases including amoebic, viral and bacterial, prion diseases, respiratory diseases, asthma, diseases of the genitourinary system, chronic obstructive pulmonary disease (COPD), cancers including breast, prostate, colon and lung cancers, and psychiatric conditions.

A treatment that is being investigated in the previous clinical trial and the new clinical trial can be any treatment designed to produce measurable outcomes in patients, either in humans or animals. A treatment can be associated with a pharmaceutical. For example, the treatment can be the administration of a new drug, a new indication for an existing drug, new or different dosing for a drug, or a different combination of a plurality of drugs. The treatment can be a new or different therapy, including therapies such as psychotherapy, physical therapy, behavioral therapy, or cognitive therapy, or the treatment can be or include a new or different device.

Step 102 of method 100 includes building one or more predictive models for predicting progression of the condition in patients. A predictive model is built to generate a prediction for future condition progression for a patient based on clinical data for the patient. Predictions can include various metrics typically used as outcomes in clinical trials. Examples of types of prediction models are regression models and time-to-event models. A regression model can predict patient ability or condition state at a point in time in the future, while a time-to-event model determines the log likelihood that a patient will reach a certain ability (disability) or condition state, including death.

FIG. 2 provides examples of regression models and time-to-event models for ALS patients. Each of the models is associated with a clinical metric that clinicians may use to measure ALS progress in their patients. Each model is named according to the clinical metric that it is designed to predict. For example, the ALSFRS-R total score is a functional rating score for ALS. The test for generating this score includes 12 questions that relate to the ability to perform a task. Patients are rated on their ability to perform a task on a point scale (e.g., a five-point scale from 0=can't do, to 4=normal ability). Individual item scores are summed to produce a total score (e.g., 0=worst and 48=best). The ALSFRS-R model can predict an ALSFRS-R score at a defined time in the future (for example, in 6 months, in 1 year, in 5 years, etc.) for a patient based on clinical data for the patient.

Another example, of a predictive model for ALS is the "50% vital capacity" time-to-event model, which predicts the log likelihood that a patient reaches 50% vital capacity. Vital capacity is a clinical measure of the volume of air that a patient can expel. Fifty percent vital capacity is a commonly used milestone in ALS that is often used to prescribe non-invasive ventilation. Similarly, a "% expected VC" regression model predicts the percent expected VC at a defined point in the future.

Any of numerous predictive modeling techniques known to those of skill in the art can be used to create the predictive model, including regression and machine learning techniques. Regression techniques could include, but are not limited to, linear regression, logistic regression, Cox proportional hazards model, time series models, classification and regression trees and multivariate adaptive regression splines. Machine learning techniques could include k-nearest neighbors, deep learning algorithms, convolutional neural networks, support vector machines, or naïve Bayes. These modeling techniques can be used to perform variable reduction in order to select the most predictive feature set followed by building a working predictive model. Models can be combined using known methods to produce ensemble models with possible increased accuracy.

The one or more predictive models may be built by training a learning machine on clinical data of patients having the condition for which the predictive model is built. The clinical data may be obtained from one or more databases 140 of historical clinical data collected from individual patients. This data generally captures how each patient's disease progressed over time. Data may include vitals such as height, weight, pulse, and forced vital capacity, genetic data, biomarker data, disease progression scores, dates of events such as symptom onset, date of diagnosis, date of death, gender, age, smoking and drinking habits, medication usage, occupation, and any other types of relevant information. An example of a database that stores historical clinical data is the PRO-ACT database of ALS patients, which includes data collected from over 10,700 ALS patients from completed ALS clinical trials.

Examples of other clinical information databases include the heart disease database and the diabetes database maintained by the University of California Irvine. The "All of Us" general patient database maintained by the NIH is another example. Archived clinical research datasets, such as those available from NIH, can be used. Individual datasets can be either used separately as "Clinical Trial Datasets" for testing or merged to form large disease datasets for model training. Models can be built using the CODR (Critical Path Institute) and/or ADNI Alzheimer's disease datasets for Alzheimer's treatment trials. Models can be built using the PPMI Parkinson's disease data base available from MJ Fox Foundation for Parkinson's treatment trials. Models for cancer treatment trials can be built using the Cancer Genome Atlas (TCAG). Models for type 1 diabetes treatment can be built using the TEDDY type 1 diabetes dataset.

A predictive model can be built to predict any outcome of interest to a user, including outcomes useful as primary or secondary endpoints to measure the efficacy of drug candidates, including continuous outcomes and classification outcomes. Useful outcomes could measure survival, disease recurrence, a clinical measure such as vital capacity or a lab value such as cholesterol or serum glucose level, or the results of a diagnostic test such as an angiograph, or a biomarker indicative of disease progression or severity. Other models could predict outcomes considered as being wider indicators of disease burden, such as absence from work, or patient centered outcomes, such as quality of life measures and functional status.

Preferred embodiments would be predicted outcomes useful in ALS clinical trials, including time to event outcomes such as survival, time to 50% vital capacity, time to use of a wheelchair, time to loss of speech, and time to use of a feeding tube or regression outcomes such as ALSFRS-R functional score, or the ALSFRS-R sub-scores (including bulbar score, respiratory score, fine motor score and gross motor score) or percent expected vital capacity, or vital capacity in liters.

Another preferred outcome would be the prediction of the ADAS-Cog score and or activities of daily living, global severity, or global change ratings, or Mini Mental State Examination (MMSE) by an Alzheimer's disease model. In Parkinson's disease, primary outcomes could be the prediction of the Unified Parkinson's Disease Rating Scale (UPDRS) or any of its subscores, or Parkinson's Disease Cognitive Rating Scale (PD-CRS), Montreal Cognitive Assessment (MoCA), Scales for Outcomes in PD Cognition (SCOPA-COG), Mini Mental State Examination (MMSE), Mattis Dementia Rating Scale (MDRS) in a Parkinson's disease model.

In some embodiments, clinical data from a disease database is reformatted and/or screened prior to being used to train the predictive model. The data in the database may have been collected by different parties at different times using differing clinical techniques, and therefore, may be not be suitable in its raw form. Therefore, the data may need to be harmonized or screened for generating training data having a consistent content and/or format from one patient to the next. This can include simple tasks such as harmonizing date formatting and measurement units and can include more involved tasks such as determining a version of a clinical test used to generate a score for a test that has changed over time. Some individual data points may be imputed using any of a variety of methods known to practitioners in the field. Reformatting and/or screening of the clinical data used for training may be an automated task or may involve the participation of one or more personnel, such as one experienced with the clinical disease evaluation process, to make judgments about the reformatting or screening of data in a given patient record or set of patient records.

At step 104 a predictive model 150 is selected for analyzing data generated during a clinical trial for a treatment for a condition. In some embodiments, the predictive model is selected from among a set of available predictive models. The predictive model 150 may be selected based on the type of condition and based on the desired outcome of the treatment. For example, for a clinical trial conducted to evaluate the effectiveness of a drug designed for prolonging life in ALS patients, a predictive model for predicting time to death for ALS patients may be selected, or for a clinical trial for a drug designed to slow the decline in functional impairment in ALS patients, a predictive model for predicting ALSFRS-R score may be selected.

According to some embodiments, a method for enrolling candidates in a new clinical trial based on data from a previous clinical trial may not include step 102 and/or step 104. One or more predictive models may have already been built at a previous time. One or more preexisting models may have been provided by a third-party, such as via a purchase or public release. In some embodiments, a user may select a pre-existing predictive model from among a set of available models (e.g., selecting an ALS predictive model for analyzing an ALS clinical trial from among predictive models for a number of diseases). In other embodiments, a user does not select a predictive model; instead, the predictive model may be a default or otherwise preselected model.

At step 106, patient baseline records for patients that participated in a previous clinical trial are extracted from a clinical trial database 160. The patient baseline records may include any patient data that was generated prior to the patients receiving the clinical trial treatment or placebo. The baseline data may be data used to screen the patients for enrollment in the previous clinical trial or any other patient information. The patient records may be received from a third party, such as a third party that conducted the clinical trial, or may be retrieved from a local database or a publicly available database of individual trials. The patient baseline records generally include records for patients in the control arm(s) and patients in the treatment arm(s).

At step 108, patient baseline records from the previously conducted clinical trial are fed into the predictive model 150 to generate predictions for patients in the previously conducted clinical trial. As noted above, the predictive model 150 was built by training a learning machine on historical clinical data for patients having the condition, and therefore, predictions for the patients in the previously conducted clinical trial are generated based on clinical data for patients that were not in the clinical trial—the patients whose data was used to build the predictive model.

The output of the analysis of the patient baseline records using the predictive model 150 is a set of prediction data that indicates the predicted progression of the condition for the patients in the previously conducted clinical trial. For example, for a predictive model configured for predicting the ALSFRS-R score one year from enrollment in a previously conducted clinical trial for testing the efficacy of a drug for treating ALS that included 100 trial patients, the prediction data includes 100 predicted ALSFRS-R scores—a predicted ALSFRS-R score for each patient in the previously conducted clinical trial. In some embodiments, prediction data includes likelihoods of a certain milestone being reached. For example, the prediction data can include the likelihood that a patient has a time-to-death of 10 years or the log likelihood value itself.

At step 110, the clinical trial patient data is grouped into a plurality of subsets based on the prediction data. Each subset corresponds to a subgroup of patients in the clinical trial. The effectiveness of the treatment is evaluated for each subgroup by analyzing the corresponding subset of data. The subsets of clinical trial patient data are associated with subgroups of trial patients that have similar predictions within certain bounds. For example, a subset of data can include the data for patients having a prediction value in the range of 1 to 1.5. In some embodiments, subsets of data are selected based on percentages of patients in the associated subgroups. For example, three subsets of clinical data may be defined in which each subset is associated with a third of the clinical trial patient population. The one-third subgroups for each data subset are each comprised of patients having a continuous range of predicted values. So, for instance, a first subgroup includes patients having predicted values ranging from 0.0 to 0.5, the second subgroup includes patients having predicted values ranging from 0.5 to 1.0 and the third subgroup includes patients having predicted values ranging from 1.0 to 1.5. Subsets may be defined for any size subgroup. For example, subsets may be associated with subgroups having 50%, 25%, 10%, 5%, 2% or any other percentage of the clinical trial population. Subsets need not be mutually exclusive of one another. For example, a first subgroup includes patients having predicted values ranging from 0.0 to 0.5, the second subgroup includes patients having predicted values ranging from 0.0 to 1.0 and the third subgroup includes patients having predicted values ranging from 0.0 to 1.5.

The subsets of clinical trial data include the trial outcome data generated during the clinical trial—i.e., the data that reflects the effect or lack thereof of the treatment and placebo. Thus, the clinical trial data includes measures of patient condition associated with the conduct of the clinical trial. Each subset includes data for patients that were administered the treatment during the clinical trial and may also include data for control patients, such as those administered a placebo. The clinical trial outcome data may be extracted from the clinical trial database at step 112.

The effectiveness of the trial on the patients in a subgroup is evaluated by analyzing the data in the associated subset of clinical trial patient data. For example, the clinical trial outcomes measured during the clinical trial are compared between the treatment group and the control group to generate a measure of efficacy of the treatment. The measure of efficacy for any given subgroup may be less than, equal to, or greater than a measure of efficacy for the full analysis set—the full set of data for which the success of the previously conducted clinical trial was judged. The measure of efficacy may be, for example, a probability value (p-value) or any other suitable value for measuring the efficacy of a treatment in a clinical trial, or more generally, the outcome of a study.

At step 114, measures of efficacy for the subsets of clinical trial data are queried to identify one or more subsets of clinical data (corresponding to subgroups of patients) that show a different (e.g., higher) measure of efficacy relative to the full analysis set. This identification may include determining whether any of the measures of efficacy are above or below a threshold value. For example, the success of a clinical trial may be judged based on whether there is a statistically significant difference between the treatment arm and the control arm based on a p-value equal to or below 0.05, and the p-values for the subsets of data may be searched for values that are equal to or below 0.05.

To the extent that any subgroups of patients generated improved, or sufficiently improved, outcomes relative to the full data set, the conclusion can be reached that the patients in the subgroup of patients share common characteristics that lead to detectable results. The subgroups are generally more homogeneous in one or more characteristics than the full patient group, and the homogeneity of the members of a subgroup associated with a sufficiently high efficacy measure contributes to the detectable effect of the subgroups relative to the full patient group. The detectable outcome for the identified subgroup can be due to improved effect of the treatment on the patients in the group—for example, the treatment works better on patients having a given characteristic than patient lacking the characteristic. The detectable outcome for the identified subgroup can also be due to the removal of noise in the data, i.e., lowering of the RMSE. As an example, patients with rapidly progressing diseases relative to the other patients in the clinical trial can cause high variance (e.g., high RMSE) in the clinical outcome data, leading to an inability to show a statistically significant outcome from the treatment. A subgroup lacking these patients can show a statistically significant outcome where the full analysis set does not. Thus, for example, the treatment effect in the full group and a subgroup might be the same, but the RMSE in the subgroup might be less than the full group to the extent that the p-value for the effect size of the subgroup is less than 0.05 when the p-value for the effect size of the full group is not. An improved effect size associated with a subgroup may be due to a combination of an increased treatment effect and reduced noise.

At step 116, one or more prediction values associated with the one or more subsets showing improved results relative to the full analysis set (e.g., those that have a p-value below 0.05) are identified and established as future clinical trial patient enrollment screening criteria. The one or more prediction values can be used to screen candidates for a future clinical trial for the treatment, as discussed further below. The one or more prediction values are the prediction values that were used to define the identified subset. For example, a subset of clinical trial data identified as showing a detectable effect of the treatment may include the data for patients having a predicted progression value in the range of 0.5 to 1.0. These upper and lower predicted condition progression values for the identified subset of clinical trial data are established as upper and lower screening thresholds for screening candidates for a future clinical trial. In some embodiments, the method ends with the screening criteria being provided to a user for the user to use in designing a future clinical trial.

According to some embodiments, the method includes screening candidate patients for enrollment in a future clinical trial. At step 118, clinical data is received for screening the associated patient for enrollment in a future clinical trial for the same treatment. This clinical data can be received from a clinician that generated some or all of the clinical data or from a third party that collected the data from clinicians. For example, a doctor specializing in ALS treatment may enter clinical data that she generated for one or more of her patients into a candidate screening portal to determine whether one or more of her patients should be enrolled in a clinical trial, or a drug development company planning a future clinical trial may collect candidate patient information for providing to the screening process.

At step 120, one or more condition progression prediction values are generated for the candidate patient by feeding the candidate's clinical data into the predictive model 150 (i.e., the same predictive model used to generate the predictions for the previously conducted clinical trial). So, for example, where the predictive model 150 was used to generate ALSFRS-R scores for the patients in the previously conducted clinical trial, step 120 generates an ALSFRS-R score for the candidate patient.

At step 122, the candidate patient's prediction value(s) from step 120 are compared to the future clinical trial patient enrollment screening criteria established at step 116 to determine whether the candidate patient should be enrolled in the clinical trial. If the candidate patient's prediction value(s) meets the criteria, then the candidate is identified for enrollment in the clinical trial. If the candidate patient's prediction value(s) fails to meet the criteria, then the candidate is identified for rejection for enrollment in the clinical trial.

In some embodiments, the screening criteria may be upper and lower prediction value thresholds and candidate patients that have a prediction value that falls in the range defined by the upper and lower prediction value thresholds may be identified for enrollment in the clinical trial and those whose prediction values are outside of the range are identified for rejection from enrollment in the clinical trial. In some embodiments, the screening criteria may include just an upper threshold or just a lower threshold, so that a candidate patient's prediction value need only be below or above, respectively, the threshold to be identified for enrollment in the clinical trial.

Steps 118 through 122 may be repeated for any number of candidate patients. At step 124, the clinical trial is enrolled with the patients selected for enrollment. At step 126, the clinical trial is conducted and enrolled patients may be given treatments or placebos, according to well-known clinical trial methods. In some embodiments, enrolled patients are given different levels of treatments based on the screening—e.g., the clinical trial may be defined to include low dose and high dose arms and the screening may have identified which patients should be included in which arm.

At the end of the clinical trial, the trial outcome is determined. The trial outcome may show a detectable treatment effect that was not detectable in the previous clinical trial, which may be due to the screening of candidate patients based on the results of the previous clinical trial, as discussed above. As a result of method 100, the treatment developer may have the evidence to proceed with further treatment development or to receive approval from an approval authority, such as the Food and Drug Administration, when the treatment would have otherwise been abandoned due to the failure of the first clinical trial. This could help prevent the loss of a considerable investment in the development of the treatment and increase the number and quality of treatments available to patients, which could improve quality of life, relieve suffering, and prolong life.

FIGS. 3A-3D illustrate one technique for identifying a subgroup of patients associated with an improved treatment effect relative to the full analysis set of 1,373 subjects that can be used to establish screening criteria for screening candidates for a future clinical trial. This technique could be used, for example, in step 114 of method 100. In this technique, clinical trial outcome data from the previously conducted clinical trial is grouped into subsets based on subgroups of patients, and the treatment effect, root mean square error (RMSE), and effect size are determined for each subset. The effect size is used as the measure of efficacy of the treatment for a subgroup of patients corresponding to the respective subset and is equal to the treatment effect divided by the RMSE. The members of the subgroups that define the data subsets are selected based on the predicted condition progression data generated using the predictive model (e.g., prediction data generated in step 108 of method 100). A subgroup associated with an increased effect size may represent a patient population for which a future clinical trial may show a detectable or improved treatment outcome relative to the previously conducted clinical trial, and therefore, the predicted condition progression data for such a subgroup may be established as screening criteria for future clinical trial candidate patients.

FIGS. 3A-3D are graphs of treatment effect, root mean square error, effect size, and p-value, respectively, for a given subset as a function of the proportion of total population of the previously conducted clinical trial in the subgroup corresponding to the subset. Each data point on the charts represents the respective metric for the given subgroup. The groups are defined according to "low risk," "moderate risk," and "high risk" predictions of condition progressions. In the illustrated example, the predicted progression metric is 50% expected VC risk for ALS patients, but the illustrated concept is applicable to any metric.

On the left-hand side of each graph, the proportion of the population in each group is one-third, which is the smallest group size used in the illustrated embodiment. However, any group size may be used. The low risk group 302 includes the third of the population with the lowest expected 50% VC risk, the high risk group 304 includes the third of the population with the highest expected 50% VC risk, and the moderate risk group 306 includes the remaining third of the population. The respective metric for each group is plotted. Moving toward the right of each chart, the sizes of the respective groups are increased to include more patients in the effect analysis until the entire population is included. The size of the low risk group is increased initially by including members from the low end of the moderate risk group, the size of the high risk group is increased initially by including members from the high end of the moderate risk group, and the size of the moderate risk group is increased by incorporating members from both the low and high risk groups. For each increment of increased group size, the effect size is determined for the group and plotted on the respective graph. The metrics for the three groups converge to the metric value for the full analysis set ("FAS"), which represents the respective metric value for the full population.

Figure 3A:
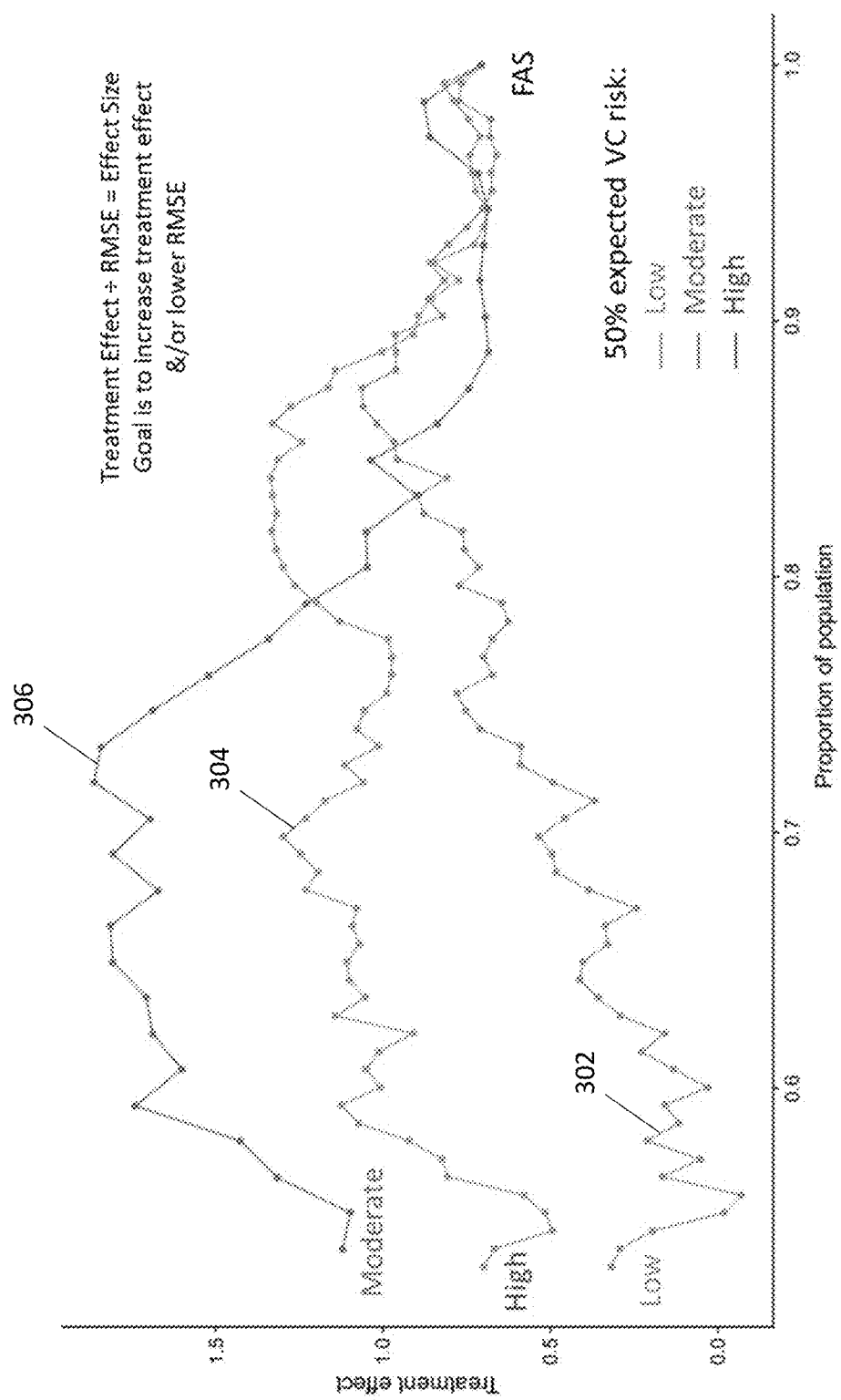
FIGS. 3A-3D are plots for identifying patient subgroups associated with improved treatment effects, according to one embodiment.
Figure 3B:
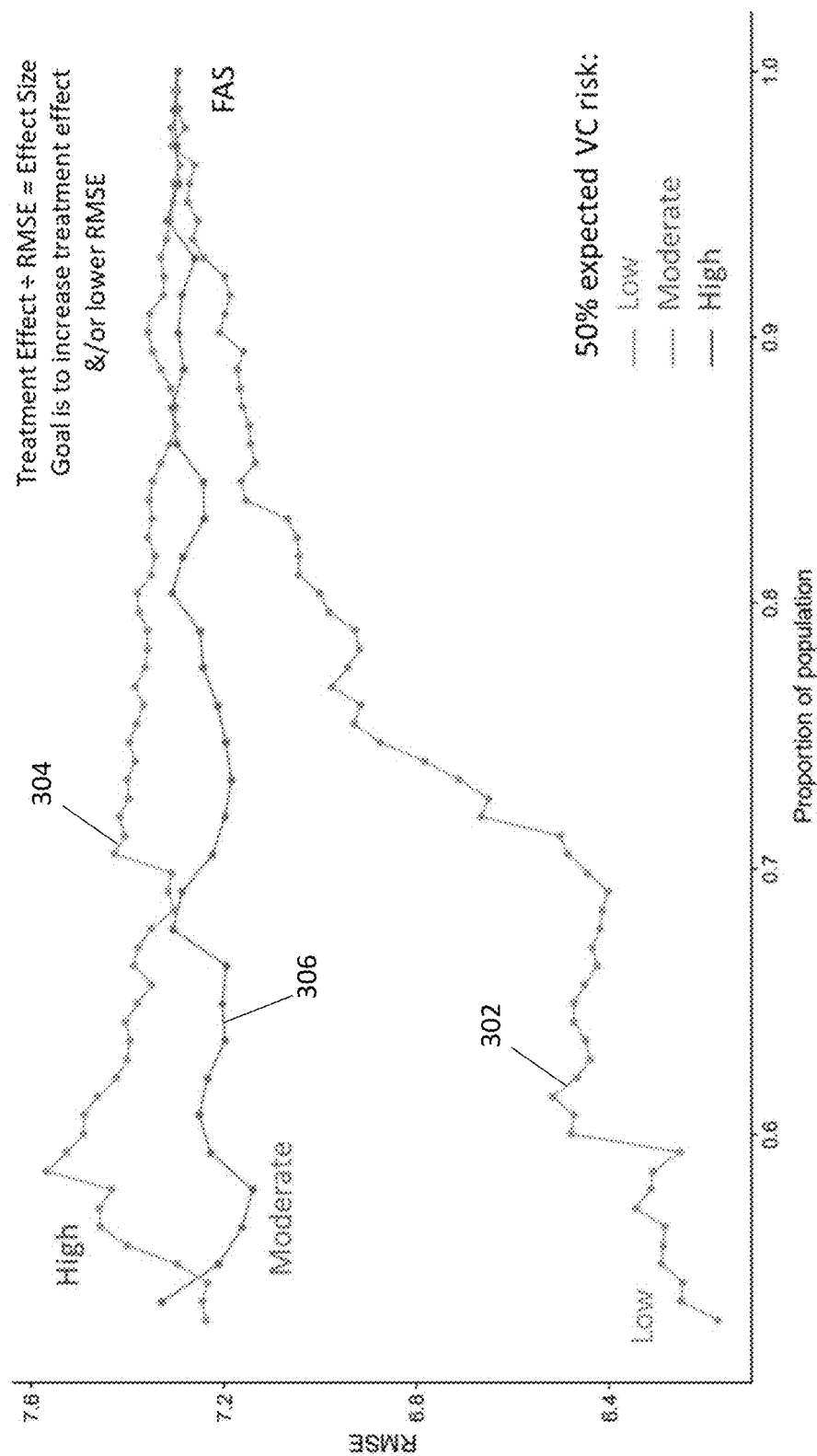
Figure 3C:
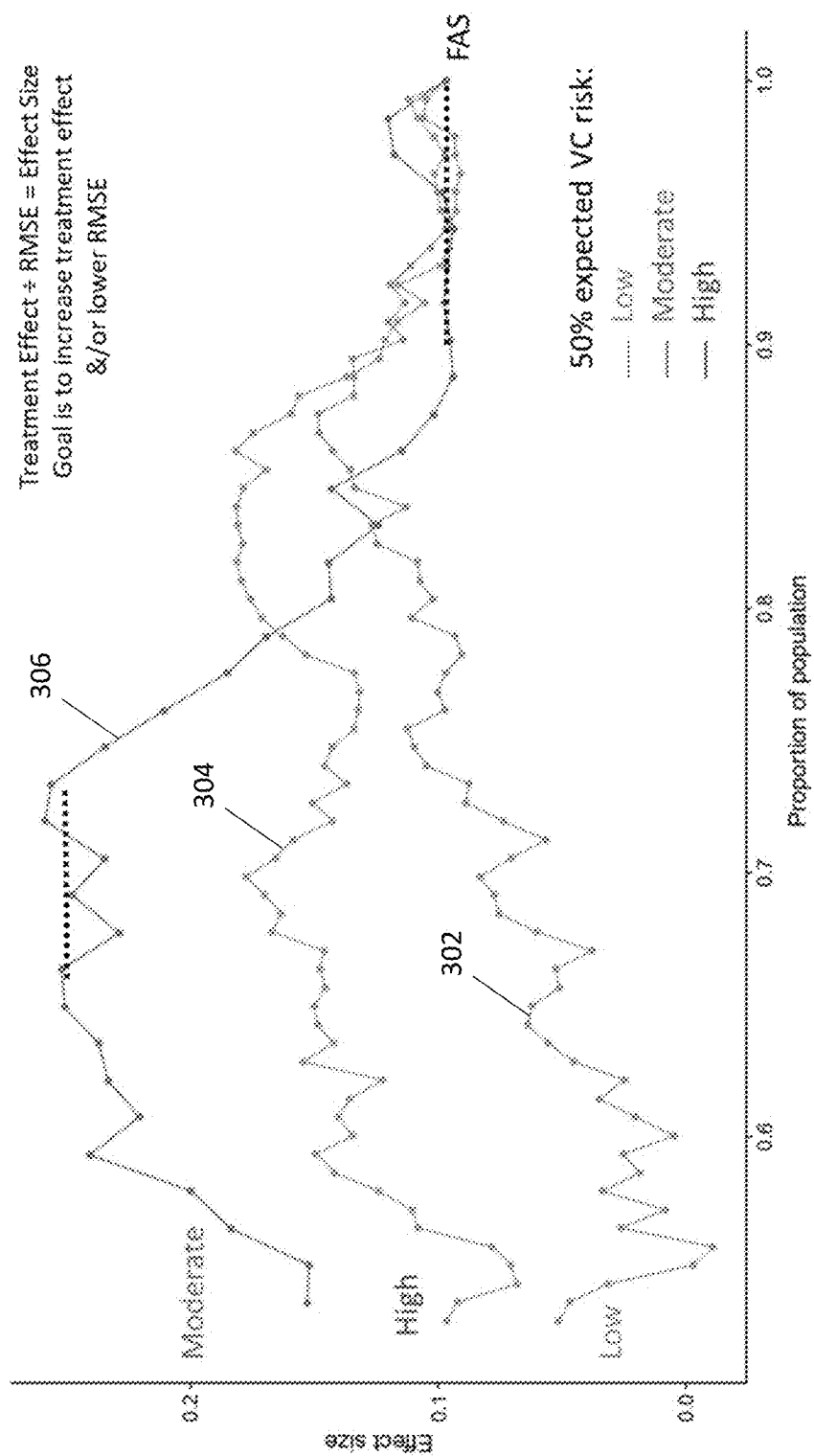

FIG. 3C shows a maximum of the low risk group 302 reached at around 80-90% of the population, which is the size at which the low risk group includes the 80-90% of the total clinical trial population having the lowest predicted condition progression values. While the effect size of this subgroup is less than the effect size of the moderate 33% of the population, this subgroup represents just under ninety percent of the population, which can mean that using the prediction data for this subgroup as screening criteria can mean a greater proportion of the candidates for the future trial may be selected for enrollment. The user could use this information to simulate a number of trials with the goal of determining the characteristics of a trial which would best suit the user's needs viz: a trial with a higher treatment effect that would reject many candidates or a trial with a lower treatment effect that would include many more candidate patients.

Figure 3D:
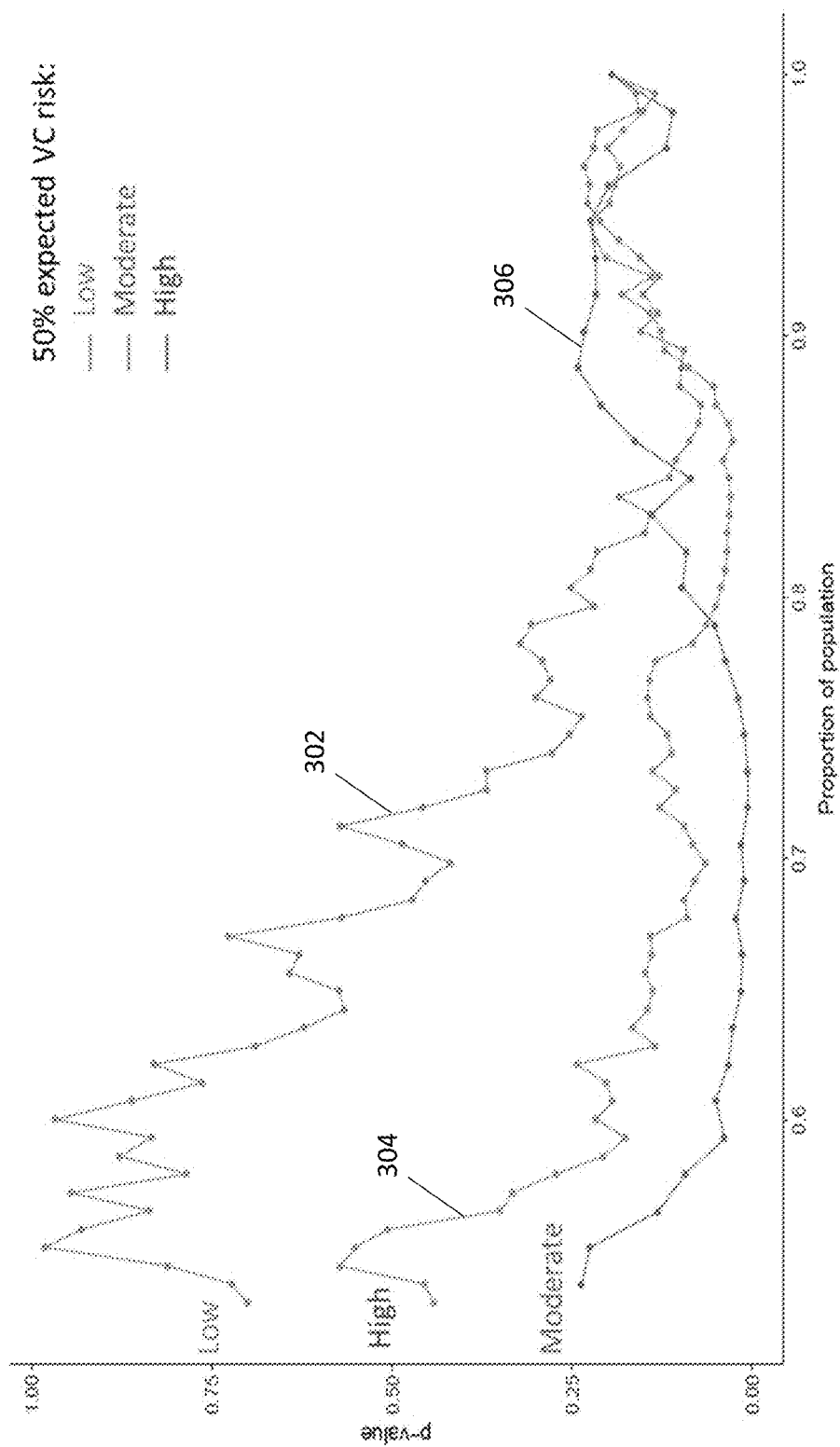

FIG. 3D shows the p-values reached for the three risk groups depicted in the FIGS. 3 A through C as determined using covariate adjusted linear regression analysis. As can be seen, only the moderate risk group 306 achieves p-values less than 0.05, and this is for sample sizes that are approximately 65% to 75% of the total sample size (1,373 in this experiment). Thus, a trial using the thresholds for the moderate risk group could be conducted with a sample size equal to 65% of 1,373, or fewer than 900 patients. This represents a significant savings in both time and money for the drug sponsor who conducts the trial.

The overlain black dashed lines in FIG. 3C indicate a leveling of the effect size for the moderate risk group at about 70% of the trial population (representing 70% of the trial population with the lowest risk predictions) and for the full analysis set. According to some embodiments, the subgroup associated with this leveling of the moderate risk group can be selected for establishing screening criteria since it is associated with the highest effect size of the subgroups analyzed and encompasses seventy percent of the trial population. The chart of FIG. 3C demonstrates that a clinical trial patient population can be divided into subgroups that are systematically adjusted in size for analysis by including the nearest individuals in a stepwise manner.

Figure 4A:
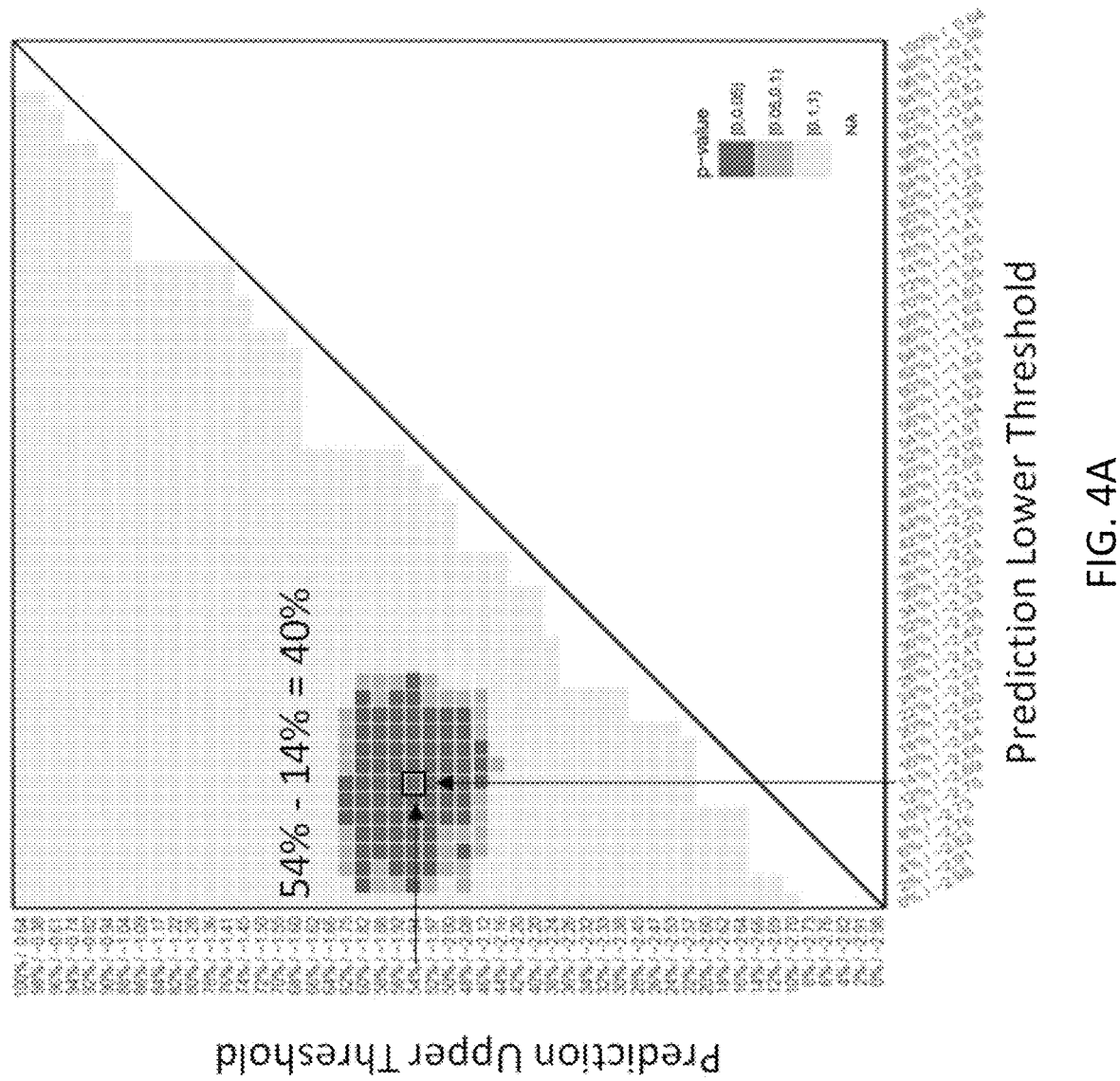

FIGS. 4A and 4B illustrate another technique for identifying a subgroup of patients associated with an improved treatment effect relative to the full analysis set that can be used to establish screening criteria for screening candidates for a future clinical trial. FIGS. 4A and 4B show "heat maps" for effect size that represent treatment efficacy metrics for previous clinical trial patient subgroups.

Each block in the heat maps represents a subgroup whose members are defined by upper and lower condition progression prediction thresholds. For each block, a statistical analysis is conducted on the clinical trial data associated with the subgroup represented by the block to determine the trial outcome for the subgroup. As explained further below, the heat maps can be used to identify subgroups that show statistically significant effect sizes (e.g., p-values of less than 0.05). Alternately, heat maps can be constructed of treatment effect and, separately, RMSE. These can then be used to identify zones with maximal treatment effects and minimal RMSE that can be used to find areas where treatment effect maximums overlap RMSE minimums. These metrics can be used to simulate sample sizes that would yield effect sizes with a p-value of less than 0.05.

The y-axis of the heat map in FIG. 4A is labeled with the upper prediction progression threshold values and the x-axis is labeled with the lower prediction progression threshold values. In the illustrated example, the prediction values are log likelihoods that range from $-2.98$ at the low end to $0.64$ at the high end. Each axis is also labeled with percentage of total clinical trial patient population. To determine the size of a subgroup in terms of percentage of patient population, the corresponding x- and y-axis values for the associated box are used. So, the upper left-hand box represents the entire patient population since it corresponds with upper and lower thresholds that capture 100% of the patient population. In other words, 100% of the patients had prediction values at or below 0.64 (the y-axis value corresponding to the upper left-hand box) and at or above $-2.98$ (the x-axis value corresponding to the upper left-hand box). For the highlighted box, the upper and lower thresholds are $-1.94$ and $-2.66$, meaning that the box represents a subgroup of patients that had prediction values ranging from $-2.66$ to $-1.94$. The size of this subgroup is 40% of the total patient population, which is derived from the chart by subtracting the population percentage corresponding to the upper prediction threshold from the population percentage from the lower prediction threshold: 54%–14%.

The black diagonal line represents the boundary where the lower threshold is below the upper threshold. Thus, the blank lower-right half represents an area that is not possible, where the lower threshold is greater than the upper threshold. The diagonal does not quite touch the area where blocks begin because the sample sizes in squares near the diagonal are too small (e.g., subgroups of only one or two patients) to be able to draw meaningful comparisons.

In the illustrated embodiment, there are three colors used to display the boxes, each of which corresponds to a p-value threshold computed from the clinical trial outcome data for the patients in the subgroup corresponding to the respective box. In this example, the p-value is used as the measure of efficacy of the treatment. Boxes corresponding to data that generates a p-value equal to or below 0.05 are colored red, those corresponding to data that generates a p-value between 0.05 and 0.10 are colored orange, and those corresponding to data that generates a p-value above 0.10 are colored yellow. The upper left-hand box in the chart of FIG. 4A (representing the full analysis set) being colored yellow shows that the clinical trial represented in this example had a low probability of a positive treatment effect, since the p-value was above 0.10. The highlighted box, on the other hand, which is red (meaning the associated p-value is below 0.05) represents a subgroup for which there is a high probability of a positive treatment outcome. This subgroup could be identified and used to establish the screening criteria for the future clinical trial. So, too, could the subgroups represented by the boxes surrounding the highlighted box, since they are also red.

FIG. 4B is a heat map according to another exemplary embodiment. In this example, the highlighted block identifies a group of patients who are described by certain prediction data (e.g., "patients who entered the trial with a predicted VC50 log likelihood between −1.87 and −0.84), among whom the patients in the treatment arm responded differently from the patients in the control arm. If this trial had been successful, the upper left corner representing the full analysis set would have been red. The area of red blocks indicates a robust "hot spot" centered at a lower threshold log likelihood of reaching 50% VC of −1.87 and an upper threshold of −0.84 (over a full range of −1.99 to +1.50). This hot spot is robust in the sense that multiple blocks in the area show the detectable effect.

The thresholds for the block in the center of the hot spot may be selected for establishing screening criteria for a future clinical trial. Thus, a future clinical trial could be designed that would include only patients whose baseline characteristics yield predictions that fall within the identified threshold boundaries. Blocks showing detectable effects (e.g., red blocks) that are close to orange or yellow blocks may not be good blocks to select for establishing screening criteria because they are close to including prediction values associated with patients that reduce the treatment effect value and/or increase the RMSE value. Therefore, according to some embodiments, a subgroup that is in the middle of a hot spot may be selected for establishing the screening criteria. On the other hand, a lone red block may be rejected. In some embodiments, a block may be selected based on the size of the corresponding subgroup. For example, for multiple adjacent blocks in the middle of a hot spot, the block corresponding to the greater size subgroup may be selected, since this would result in more expansive screening criteria, leading to more candidates being accepted for enrollment in the future clinical trial.

In some embodiments, multiple hot spots may occur and multiple subgroups may be selected for establishing multiple sets of screening criteria. For example, a block in a first hot spot corresponding to relatively low predicted metrics (e.g., patients with slowly progressing disease) may be identified to establish the screening criteria for a low dosage arm of a future clinical trial and a block in a second hot spot corresponding to relatively high predicted metrics (e.g., patient with rapidly progressing disease) may be identified to establish the screening criteria for a high dosage arm of the future clinical trial (i.e., more aggressive treatment).

Figure 5:
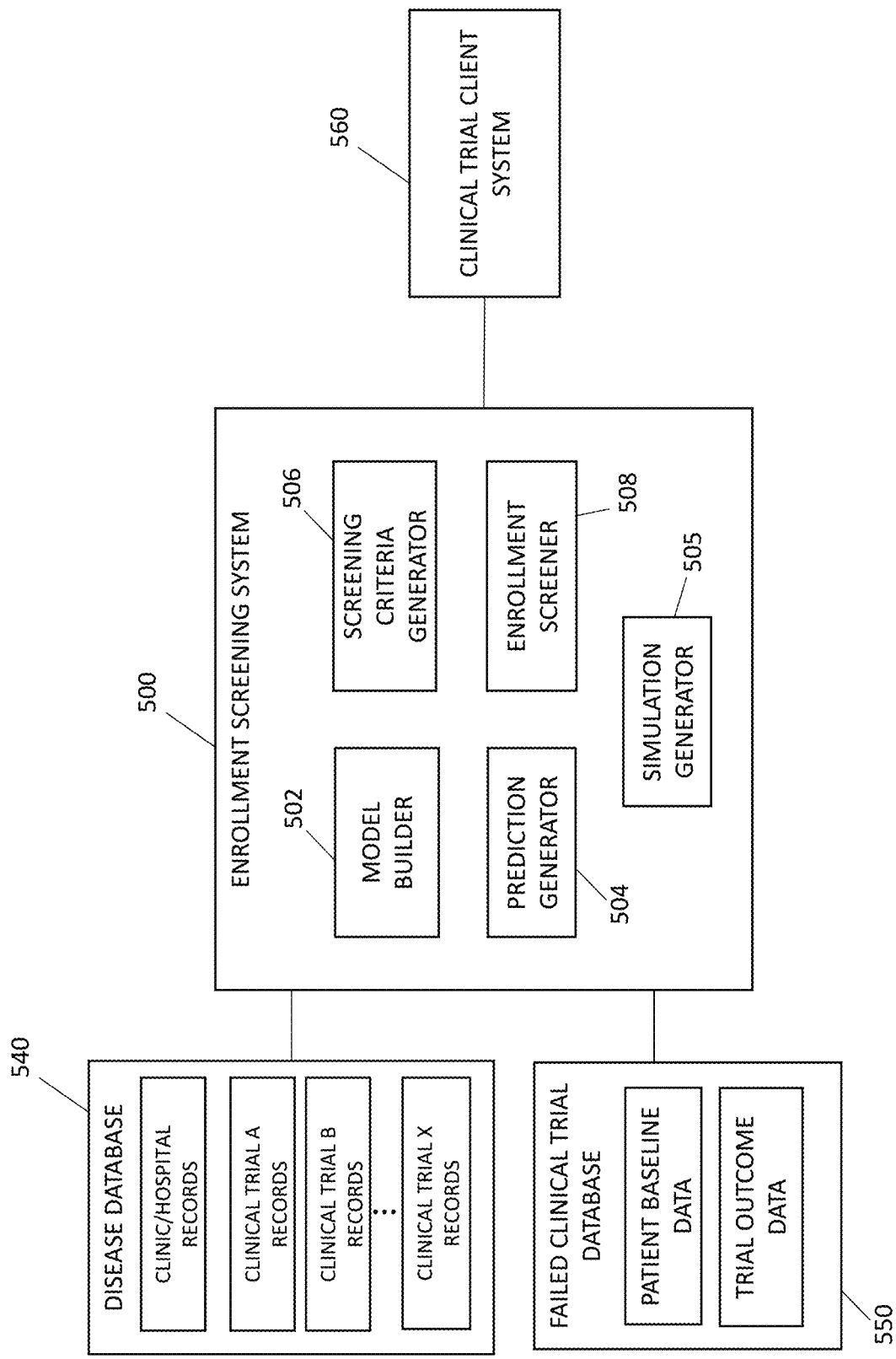
FIG. 5 is a functional block diagram of a system for enrolling candidates in a clinical trial based on patient-level predictions, according to some embodiments.

FIG. 5 is a functional block diagram of an enrollment screening system 500 that can be used for determining which candidate patients should be enrolled in a future clinical trial for a treatment that has already been through a previous clinical trial, according to the principles and methods discussed above. System 500 may be used to perform method 100 discussed above. System 500 may include one or more servers executing one or more computer programs stored on one or more non-transitory computer readable media. System 500 may be communicatively connected with one or more of a disease database 540, a clinical trial database 550, and a clinical trial client system 560.

System 500 includes functional units such as a model builder 502, a prediction generator 504, a screening criteria generator 506, and an enrollment screener 508. These functional units represent functional components of one or more executable software programs executed by one or more processors of system 500. In some embodiments, a simulation generator 505 can be used to allow users to find the correct sample size for zones with high treatment effect and/or a low RMSE with sample sizes too small to test the significance of the effect size. The simulation generator 505 can be useful in finding hot spots in relatively small clinical trials.

Model builder 502 is configured to build one or more predictive models for predicting progression of a condition in patients. Model builder 502 may include one or more learning machines that can be trained to predict the condition progression of a patient based on the patient's clinical records. Model builder 502 may build a predictive model for a condition by training a learning machine on training data comprised of historical clinical data gathered from patients having the condition.

This data may be retrieved from disease database 540 (such as database 140 described above with respect to method 100), which may be a third-party database or a local database that maintains clinical information for patients suffering from the condition. The disease database 540 may include patient data from clinics, hospitals, research institutions, government institutions, or any other suitable source of patient data. The disease database 540 may include patient clinical data from previously conducted clinical trials or studies. Clinical trials and studies may include trials and studies related to any number of various treatments and study topics related to the disease. Patient clinical data may also come from patient registries, which generally are databases of observational patient data, not from an interventional clinical trial. Many patient organizations are creating these types of databases. Patient data may be collected from other data sources, including private non-EHR data aggregators like PATIENTSLIKEME (https://www.patientslikeme.com) and APPLE'S IOS HEALTH KIT (https://developer.apple.com/healthkit/) and GOOGLE FIT (https://developers.google.com/fit/).

Model builder 502 builds a model for generating predictions of one or more clinical metrics that clinicians may use to measure condition progress in their patients, as discussed above with respect to step 102 of method 100. In some embodiments, model builder 502 builds a predictive model that generates predictions for a single metric of disease progression, and in other embodiments, model builder 502 builds a predictive model that generates predictions for multiple metrics of disease progression.

In some embodiments, model builder 502 is configured to reformat, filter, screen, or otherwise manipulate the historical clinical data prior to training the predictive model. Model builder 502 may be configured to facilitate such manipulation by a user, such as by enabling a user to select data for inclusion in a training dataset. In some embodiments, model builder 502 may be configured for manipulating the historical data through one or more automated functions. For example, model builder 502 may automatically extract patient clinical data needed for training the predictive model and discard data that is not needed and/or reformat data based on a predefined training data schema.

In some embodiments, system 500 includes one or more stored predictive models that have been previously built, rather than a model builder for building the predictive models. These predictive models may have been previously built by system 500 or may be provided by a third party. Model builder 502 can also be configured to select a predictive model for use in screening candidates for a future clinical trial based on a past clinical trial. For example, a past clinical trial may have been conducted to test the efficacy of a new drug on prolonging the life of patients with a given disease, and a predictive model for predicting the time-to-death of patients with the given disease can be selected from model builder 502.

Prediction generator 504 is configured to generate predictions for disease progressions for patients that participated in a previous clinical trial. The prediction generator uses a predictive model built or selected by model builder 502 and patient baseline data from the previous clinical trial. Prediction generator 504 may be configured to receive the patient baseline data from previous clinical trial database 550, which stores patient clinical data for the previous clinical trial, or may be configured to extract patient baseline data from the previous clinical trial patient records received from the database 550. The database 550 may be a local or remote database and generally includes baseline data that was collected for each patient that participated in the previous clinical trial prior to the trial and trial outcome data that was collected during and/or at the conclusion of the clinical trial. This data may include treatment arm and control arm data. Prediction generator 504 uses only the patient baseline data to generate the predictions.

Prediction generator 504 generates a set of prediction data that is a function of the predictive model used and the patient baseline data. This data may include a value for a predicted disease progression metric for each patient in the patient baseline data. So, for example, where a previous clinical trial consisted of 100 patients, the prediction data generated for the trial may be 100 disease progression prediction values. In some embodiments, the prediction generator 504 executes more than one predictive model or executes a single predictive model that generates more than one metric, resulting in a prediction dataset that includes multiple prediction metrics for each patient.

Screening criteria generator 506 is configured to group clinical trial patient data into a plurality of subsets that correspond to subgroups of patients. The subsets are defined based on the prediction data generated by prediction generator 504. Screening criteria generator is configured to analyze the clinical trial data within each subset to determine the effectiveness of the treatment when considering only the data associated with patients in the corresponding subgroup of patients. Screening criteria generator 506 may generate any number of relevant subgroups having any relevant size. In some embodiments, screening criteria generator receives an input from a user for defining a minimum subgroup size and/or a subgroup size increment. For example, a user may define 5% of the total population as being the minimum subgroup size and/or may define a 5% increment in subgroup size.

Screening criteria generator 506 is configured to analyze each subset of data to generate a measure of efficacy of the treatment for the patients in the associated subgroup of patients. The screening criteria generator 506 may be configured to establish screening criteria for the future clinical trial for the treatment by identifying a subgroup associated with a measure of efficacy that is higher than a measure of efficacy of the treatment for the full first group of patients. For example, the screening criteria generator may identify a subgroup associated with a p-value of less than or equal to 0.05 where the p-value for the full trial population was above 0.05.

In some embodiments, the screening criteria generator 506 is configured to facilitate user identification of the subgroup or subgroups that establish the screening criteria. For example, the screening criteria generator may generate plots, such as those shown in FIGS. 3A-D and 4A-B, that may allow a user to identify the promising subgroup or subgroups.

In some embodiments, the screening criteria generator 506 is configured to establish the screening criteria by selecting a subgroup or subgroups, as explained above, and using the disease progression prediction value bounds for the subgroup for the screening criteria. For example, for a selected subgroup comprising the patients having a disease progression prediction value in the range of 0.0-0.5, the screening criteria may be the range of 0.0-0.5, such that candidates for the future clinical trial must have disease progression prediction values of between 0.0 and 0.5 to be enrolled in the future clinical trial. In some embodiments, the screening criteria generator may be configured to establish screening criteria for determining a sub-analysis grouping for a candidate. For example, screening criteria may be established for screening candidates into low and high dosage groupings for the trial.

The enrollment screener 508 is configured to screen candidates for enrollment in the future clinical trial. The enrollment screener 508 may be configured to receive candidate patient information and may use the predictive model used by the prediction generator 504 to generate one or more disease progression prediction values for the patient. In some embodiments, the candidate patient information is received from a future clinical trial client system 560 that can be used by, for example, a clinician to screen the clinician's patients for enrollment in the future clinical trial.

The enrollment screener 508 may be configured to determine whether the prediction value(s) for the candidate meets the enrollment criteria established by the screening criteria generator. For example, the enrollment screener may determine whether the disease progression prediction for the candidate falls within the range of prediction values established as the screening criteria. The enrollment screener may be configured to provide a notification to the future clinical trial client system 560 of whether the candidate should be enrolled in the future clinical trial. In some embodiments, the enrollment screener 508 is configured to determine a sub-analysis grouping for the candidate. For example, the enrollment screener 508 may determine that the candidate should be enrolled in a "low dose" grouping for the future clinical trial.

The future clinical trial client system 560 may be a system that is remote from the enrollment screening system 500 and communicatively coupled to the screening system via, for example, the internet. The client system 560 may be a computer that enables a user to send data to and receive data from the screening system 500. For example, the client system 560 may be a computer in a clinician's office running a web browser that is communicating with a web server of the screening system 500.

Figure 6:
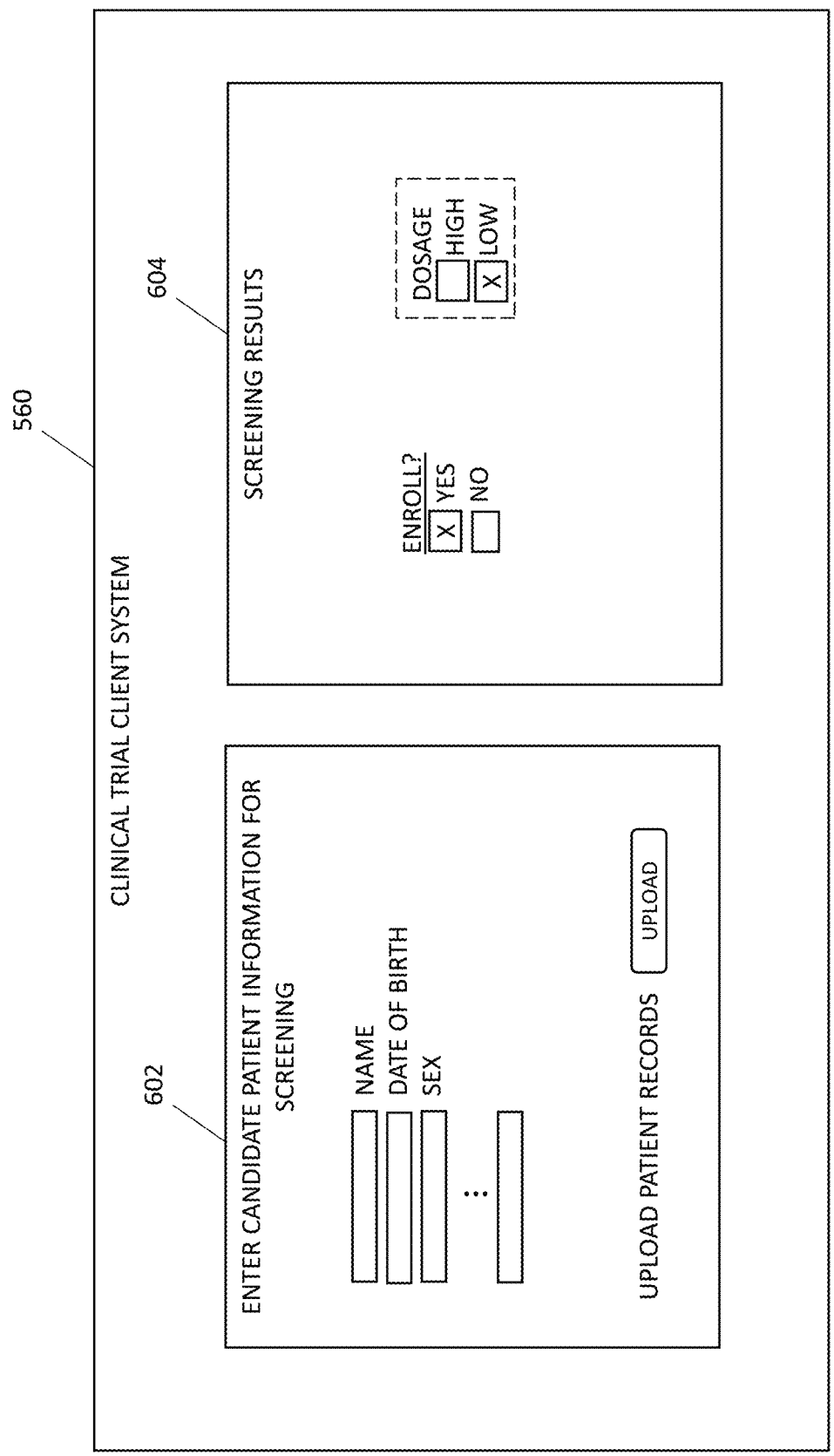
FIG. 6 illustrates exemplary user interfaces that can be used by a user for screening and enrolling candidates in a clinical trial, according to some embodiments.

FIG. 6 illustrates exemplary future clinical trial client system user interfaces for use by a clinician to provide candidate information to and receive screening results from the screening system 500, according to some embodiments.

User interface 602 is an exemplary embodiment of a user interface for a user (e.g., a clinician) to enter candidate patient information for screening. A user, such as a clinician, may enter the candidate's clinical information manually, may upload the candidate's clinical records, or may do some combination of both. In some embodiments, the party uploading the candidate information is the party that generated the patient information, such as the candidate's doctor or doctor's staff. In some embodiments, the party uploading the candidate information may be a third party that previously gathered candidate information from one or more clinicians that generated the data.

User interface 604 provides the results of the screening for the candidate. These results may include whether or not to enroll the patient in the future clinical trial and/or a grouping for the patient within the clinical trial (e.g., the patient should be enrolled in the low or high dosage arm). In some embodiments, the screening results may include an indication of the future clinical trial, such as where multiple future clinical trials are being designed. In some embodiments, the screening results are not provided to the user that originated the candidate information, but instead, to a third party that is designing and/or will be conducting the future clinical trial. The party that receives the screening results may be the party that uses or otherwise implements the screening system 500.

In some embodiments, candidate patient records are received and stored by screening system 500 for future screenings. In some embodiments, the screening system 500 provides notifications regarding candidate enrollment at a later date from when the candidate's information was provided to the enrollment system 500. For example, clinicians in the field may routinely upload patient records without knowledge of planned future clinical trials and may receive a notification from the enrollment system 500 that a candidate has been selected for a future clinical trial. The clinician may then notify the candidate to facilitate enrollment. In some embodiments, the party that provides candidate patient information is the party that receives the screening results and the party that conducts the future clinical trial.

The principles, methods, and systems described above, can be extended to a number of different applications, as will be readily recognized by one of ordinary skill in the art. Examples of application that are within the scope of the present disclosure are described further below.

Prediction based Covariate Adjustment—In this application, predictions are made at the beginning of a trial, using patient data measured before and up to the moment that the patient begins treatment (the baseline visit). Those predictions are additional baseline data ("covariates") that can be used to adjust the analysis using traditional statistical means. The more predictive a baseline covariate is of the measured outcome of the trial (the trial "endpoint" that is measured), the more the adjustment will boost the study power (the likelihood that the study will be able to detect a real treatment effect if it is there.

Prediction based Randomization—In this application, predictions are used to define multiple strata (e.g. 3 groups of predicted "fast" "average" and "slow" progressing patients). Each of these three groups has separate randomization schedules, to assign patients to various arms of the study (e.g. placebo, high dose, middle dose, low dose). By randomizing in this way, all arms of the trial should have similar proportions of "fast" "average" and "slow" patients. Additionally, because the prediction algorithm leverages dozens of input variables, the likelihood of having a confounding variable (a statistically-significant difference in that variable between two study arms) can be reduced across all of those input variables.

Prediction based Trial Enrichment—In this application, predictions are used to define a stratum (e.g. patients with a predicted progression of at least 8 points but not more than 16 points over the next 12 months) which is used as an inclusion/exclusion criterion for enrolling patients into the clinical trial. To do this, prediction data must be readily available to the site investigator when screening the patient for eligibility to participate in the study. This type of study design is useful for either predictive enrichment (enrolling patients who are predicted to respond to the treatment being tested) or prognostic enrichment (enrolling patients who are homogeneous (expected to progress in a similar way), which allows the drug effect to stand out when those patients are randomized to different trial arms).

Prediction based Virtual Controls—In this application, predictions are made for each patient who is receiving a therapy in the study, using only data collected before the moment the therapeutic treatment is delivered. Then the patient's disease progression is observed, and compared to the predicted disease course.

One or more of the above application can be combined. For example, the virtual controls application can augment a concurrent placebo control. The predictions of the virtual control are combined with to the observation data from the placebo-arm patients. This creates a larger placebo arm for comparison to the observed treatment data. Another combination may be the combination of randomization application with the covariate adjustment application. According to some embodiments, the trial enrichment application is combined with the covariate adjustment application, and in other embodiments, the trial enrichment, randomization, and covariate adjustment applications are combined.

API tool to populate prediction data into EDC systems—Clinical trials often collect their data using Electronic Data Collection (EDC) software systems. In this application, a system may host a software API that can integrate with EDC systems using a system-hosted script. This script passes data to the API, which calculates predictions and then returns them to the EDC system where they are stored. Additional applications (e.g., the applications described above and their combinations) can later leverage this data. One advantage of this application is that by collecting the prediction data at the time that data is flowing into the EDC, it can be indisputably demonstrated that all predictions were generated prospectively, without any knowledge of the patient's true progression after the drug intervention takes place.

API tool to populate prediction data into trial analysis systems—This application is similar to the preceding application except the predictions are not prospective. Instead they are made using past data, and projected forward to another time point (e.g. to present day, or to another past day).

Simulation Generator—Software platform provides users (e.g., biostatisticians at CROs or in-house at pharmaceutical companies) with the ability to simulate clinical trial designs, utilizing applications of patient predictions to optimize clinical trial design parameters. When simulating a trial, a database of historical patient data can be used for selection and simulation activities. Subsets of patients are selected from the database (at random, or otherwise), and modified with simulated treatment effects. In this application, applications described above could be packaged and provided to an end user to allow an end user to run these simulations themselves. The treatment effect and RMSE of individual cells can be used as inputs to the Simulation Generator, thus providing a way to determine sample sizes for future trials for a desired power.

Healthcare patient prognosis screening—A software system can be embedded with an EHR/EMR system of a healthcare provider.

Healthcare patient screening—A UI is built into the website of a hospital (or clinic, health system, or other healthcare provider). Prospective patients can enter their information into the form. This form sends the data to the prediction engine which returns a preliminary analysis based on limited data. Patients are then invited to make an appointment with the healthcare provider to meet with a doctor for further examination and analysis. This provides a way for the healthcare system to identify new patients who might benefit from their healthcare services Population Health—Based on predictions, a healthcare provider can understand the health of patients under her care. This will help inform whether patients are likely to experience certain health events in the near future, anticipate resource needs in an efficient way, and analyze the performance of the healthcare provider in comparison to other clinics.

Medical insurance—By predicting the likely progression of patients, and the timing of events related to their disease, medical insurance ("payers") can better anticipate and plan for cash outflows related to individual patients.

Life insurance—Unlike medical insurers, life insurance companies have access to an applicant's full medical record at the time of underwriting. Life expectancy underwriting helps the insurers price the risk of mortality for each insured person.

Life settlements (LS)—Similar to life insurance, Life Settlements (or "Viaticals") providers are investment companies who will pay an individual a cash amount today, and in exchange the LS provider will be named as the beneficiary on the insured's life policy. The LS provider also takes responsibility for making the remaining premium payments. When the insured dies, the LS provider receives the death benefit. These policies are traded among LS investment companies who hold portfolios of these policies. The value of the policy depends on the amount of the death benefit and the likely timing of the payment, which occurs when the insured dies. By better being able to estimate a patient's life expectancy, the LS provider can more easily assess the market value of these LS policies.

Figure 7:
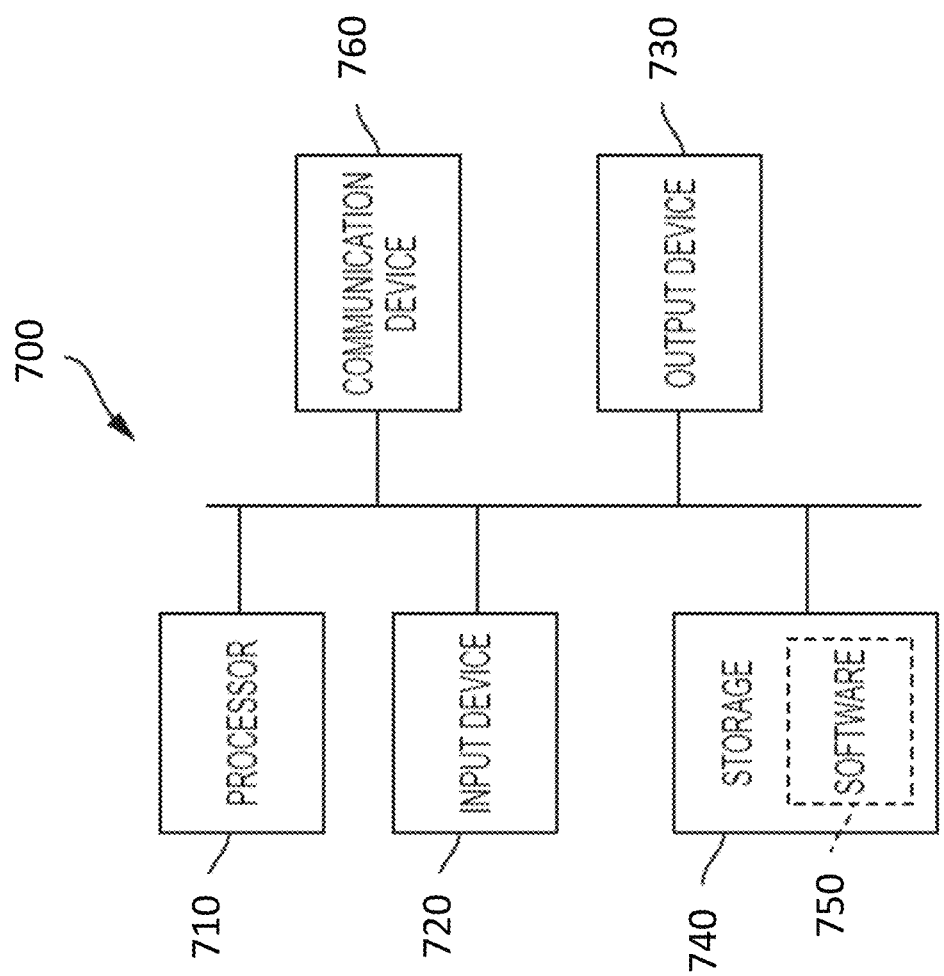
FIG. 7 illustrates a computing device, according to some embodiments.

FIG. 7 illustrates an example of a computer in accordance with one embodiment. Computer 700 can be a component of a system for displaying patient information according to the systems and methods described above, such as system 500 of FIG. 5. In some embodiments, computer 700 is configured to perform a method for displaying patient information, such as method 100 of FIGS. 1A and 1B.

Computer 700 can be a host computer connected to a network. Computer 700 can be a client computer or a server. As shown in FIG. 7, computer 700 can be any suitable type of microprocessor-based device, such as a personal computer, workstation, server, or handheld computing device, such as a phone or tablet. The computer can include, for example, one or more of processor 710, input device 720, output device 730, storage 740, and communication device 760. Input device 720 and output device 730 can generally correspond to those described above and can either be connectable or integrated with the computer.

Input device 720 can be any suitable device that provides input, such as a touch screen or monitor, keyboard, mouse, or voice-recognition device. Output device 730 can be any suitable device that provides output, such as a touch screen, monitor, printer, disk drive, or speaker.

Storage 740 can be any suitable device that provides storage, such as an electrical, magnetic, or optical memory, including a RAM, cache, hard drive, CD-ROM drive, tape drive, or removable storage disk. Communication device 760 can include any suitable device capable of transmitting and receiving signals over a network, such as a network interface chip or card. The components of the computer can be connected in any suitable manner, such as via a physical bus or wirelessly. Storage 740 can be a non-transitory computer readable storage medium comprising one or more programs, which, when executed by one or more processors, such as processor 710, cause the one or more processors to perform methods described herein, such as method 500 of FIG. 5.

Software 750, which can be stored in storage 740 and executed by processor 710, can include, for example, the programming that embodies the functionality of the present disclosure (e.g., as embodied in the systems, computers, servers, and/or devices as described above). In some embodiments, software 750 can include a combination of servers such as application servers and database servers.

Software 750 can also be stored and/or transported within any computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Computer 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 700 can implement any operating system suitable for operating on the network. Software 750 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for enrolling patient candidates in a clinical trial for a treatment for a condition, the method comprising, at a computing system:
   computing, for a first group of patients that participated in a first clinical trial for the treatment for the condition, predictions for at least one condition progress metric that indicate predicted progression of the condition for the first group of patients, wherein the predictions for the at least one condition progress metric are computed via a machine learning predictive model and clinical data associated with the first group of patients, wherein the machine learning predictive model was trained on clinical data associated with a second group of patients having the condition;
   grouping clinical trial data associated with the first group of patients into a plurality of subsets of clinical trial data based on the predictions for the at least one condition progress metric, wherein each subset of clinical trial data is associated with a corresponding subgroup of the first group of patients;
   for each subset of clinical trial data, computing a measure of efficacy of the treatment for a subgroup of patients corresponding to the respective subset;
   establishing at least one screening criteria for a second clinical trial for the treatment by identifying at least one subset of the plurality of subsets that has a measure of efficacy that is higher than a measure of efficacy of the treatment for the full first group of patients, wherein the at least one screening criteria is based on a range of values for the predictions for the at least one condition progress metric that is associated with the identified subset;
   receiving clinical data associated with a candidate for the second clinical trial for the treatment for the condition, wherein the candidate did not participate in the first clinical trial;
   computing a prediction for the at least one condition progress metric for the candidate via the machine learning predictive model and the clinical data associated with the candidate; and
   screening the candidate for the second clinical trial based on the prediction for the at least one condition progress metric for the candidate and the at least one screening criteria.

2. The method of claim 1, comprising selecting the predictive model from a plurality of different predictive models based on a goal for the treatment.

3. The method of claim 1, comprising standardizing the clinical data for the second group of patients prior to training the learning machine.

4. The method of claim 1, wherein the clinical data for the second group of patients comprises historical data for the at least one condition progress metric.

5. The method of claim 1, wherein the clinical data associated with the first group of patients is clinical data generated prior to the first trial.

6. The method of claim 1, wherein a number of patients associated with one subset is equal to a number of patients associated with at least one other subset.

7. The method of claim 1, wherein a number of patients associated with one subset is different than a number of patients associated with at least one other subset.

8. The method of claim 1, wherein the measure of efficacy of the treatment is based on the at least one condition progress metric.

9. The method of claim 1, wherein a measure of efficacy of the treatment for the full first group of patients indicates no statistically significant difference in treatment outcome between a control group and a treatment group.

10. The method of claim 1, wherein the measure of efficacy is generated by comparing treatment outcomes for control patients to treatment outcomes for treated patients.

11. The method of claim 1, wherein identifying a subset of the plurality of subsets comprises identifying a subset that has a measure of efficacy that meets a threshold test.

12. The method of claim 11, wherein the threshold test is a p-value that is no greater than 0.05.

13. The method of claim 1, wherein identifying at least one subset of the plurality of subsets comprises plotting a representation of the measure of efficacy as a function of subgroup size and the predictions for the at least one condition progress metric.

14. The method of claim 13, wherein plotting the representation of the measure of efficacy comprises generating a heat map, wherein a variation in appearance indicates a variation in the measure of efficacy.

15. The method of claim 14, wherein the heat map comprises a representation of the measure of efficacy of the treatment for the full group of patients.

16. The method of claim 14, wherein identifying at least one subset of the plurality of subsets comprises identifying a location on the heat map that is surrounded by locations having the same appearance.

17. The method of claim 1, wherein the at least one screening criteria comprises a maximum value of the range of values for the predictions for the at least one prediction progress metric and a minimum value of the range of values for the predictions for the at least one condition progress metric.

18. The method of claim 1, wherein the clinical data for the candidate is received from a clinician via a clinical trial candidate portal.

19. The method of claim 18, comprising sending an instruction to the clinician to enroll or reject the candidate for the second clinical trial.

20. The method of claim 1, wherein the range of values for the predictions for the at least one prediction progress metric comprises an upper threshold and a lower threshold.

21. The method of claim 1, wherein the at least one prediction progress metric comprises predicted patient regression or predicted time to an event.

22. The method of claim 1, wherein the patients are human and the condition is a disease.

23. The method of claim 22, wherein the disease is a neurodegenerative disease or a cancer.

24. The method of claim 1, wherein the first clinical trial is configured to determine at least one of an efficacy of a drug, an efficacy of a different dosage of a drug, or an efficacy of a different combination of drugs.

25. The method of claim 1, comprising treating the enrolled candidate with the treatment.

26. The method of claim 1, wherein screening the candidate comprises enrolling the candidate in the second clinical trial in accordance with a determination that the prediction for the at least one condition progress metric computed for the candidate satisfies the at least one screening criteria and not enrolling the candidate in the second clinical trial in accordance with a determination that the prediction for the at least one condition progress metric computed for the candidate fails to satisfy the at least one screening criteria.

27. The method of claim 1, wherein screening the candidate comprises determining a role for the candidate in the second clinical trial based on the prediction for the at least one condition progress metric computed for the candidate and the at least one screening criteria.

28. The method of claim 27, wherein determining a role for the candidate comprises determining an analysis grouping in the second clinical trial for the candidate based on the prediction for the at least one condition progress metric computed for the candidate and the at least one screening criteria.

29. A system for enrolling candidates in a clinical trial for a treatment, the system comprising one or more processors, memory, and one or more programs stored in the memory and executable by the one or more processors for:

computing, for a first group of patients that participated in a first clinical trial for the treatment for the condition, predictions for at least one condition progress metric that indicate predicted progression of the condition for the first group of patients, wherein the predictions for the at least one condition progress metric are computed via a machine learning predictive model and clinical data associated with the first group of patients, wherein the machine learning predictive model was trained on clinical data associated with a second group of patients having the condition;

grouping clinical trial data associated with the first group of patients into a plurality of subsets of clinical trial data based on the predictions for the at least one condition progress metric, wherein each subset of clinical trial data is associated with a corresponding subgroup of the first group of patients;

for each subset of clinical trial data, computing a measure of efficacy of the treatment for a subgroup of patients corresponding to the respective subset;

establishing at least one screening criteria for a second clinical trial for the treatment by identifying at least one subset of the plurality of subsets that has a measure of efficacy that is higher than a measure of efficacy of the treatment for the full first group of patients, wherein the at least one screening criteria is based on a range of values for the predictions for the at least one condition progress metric that is associated with the identified subset;

receiving clinical data associated with a candidate for the second clinical trial for the treatment for the condition, wherein the candidate did not participate in the first clinical trial;

computing a prediction for the at least one condition progress metric for the candidate via the machine learning predictive model and the clinical data associated with the candidate; and screening the candidate for the second clinical trial based on the prediction for the at least one condition progress metric for the candidate and the at least one screening criteria.

30. The system of claim 29, wherein the one or more programs stored in the memory are executable by the one or more processors for selecting the predictive model from a plurality of different predictive models based on a goal for the treatment.

31. The system of claim 29, wherein the one or more programs stored in the memory are executable by the one or more processors for standardizing the clinical data for the second group of patients prior to training the learning machine.

32. The system of claim 29, wherein and the clinical data for the second group of patients comprises historical data for the at least one condition progress metric.

33. The system of claim 29, wherein the clinical data associated with the first group of patients is clinical data generated prior to the first trial.

34. The system of claim 29, wherein a number of patients associated with one subset is equal to a number of patients associated with at least one other subset.

35. The system of claim 29, wherein a number of patients associated with one subset is different than a number of patients associated with at least one other subset.

36. The system of claim 29, wherein the measure of efficacy of the treatment is based on the at least one condition progress metric.

37. The system of claim 29, wherein a measure of efficacy of the treatment for the full first group of patients indicates no statistically significant difference in treatment outcome between a control group and a treatment group.

38. The system of claim 29, wherein the measure of efficacy is generated by comparing treatment outcomes for control patients to treatment outcomes for treated patients.

39. The system of claim 29, wherein identifying a subset of the plurality of subsets comprises identifying a subset that has a measure of efficacy that meets a threshold test.

40. The system of claim 39, wherein the threshold test is a p-value that is no greater than 0.05.

41. The system of claim 29, wherein identifying at least one subset of the plurality of subsets comprises plotting a representation of the measure of efficacy as a function of subgroup size and the predictions for the at least one prediction progress metric.

42. The system of claim 41, wherein plotting the representation of the measure of efficacy comprises generating a heat map, wherein a variation in appearance indicates a variation in the measure of efficacy.

43. The system of claim 42, wherein the heat map comprises a representation of the measure of efficacy of the treatment for the full group of patients.

44. The system of claim 42, wherein identifying at least one subset of the plurality of subsets comprises identifying a location on the heat map that is surrounded by locations having the same appearance.

45. The system of claim 29, wherein the at least one screening criteria comprises a maximum value of the range of values for the predictions for the at least one prediction progress metric and a minimum value of the range of values for the predictions for the at least one condition progress metric.

46. The system of claim 29, wherein the clinical data for the candidate is received from a clinician via a clinical trial candidate portal.

47. The system of claim 46, wherein the one or more programs stored in the memory are executable by the one or more processors for sending an instruction to the clinician to enroll or reject the candidate for the second clinical trial.

48. The system of claim 29, wherein the range of values for the predictions for the at least one prediction progress metric comprises an upper threshold and a lower threshold.

49. The system of claim 29, wherein the at least one prediction progress metric comprises predicted patient regression or predicted time to an event.

50. The system of claim 29, wherein the patients are human and the condition is a disease.

51. The system of claim 50, wherein the disease is a neurodegenerative disease or a cancer.

52. The system of claim 29, wherein the first clinical trial is configured to determine at least one of an efficacy of a drug, an efficacy of a different dosage of a drug, or an efficacy of a different combination of drugs.

53. The system of claim 29, wherein screening the candidate comprises determining to enroll of the candidate in the second clinical trial in accordance with a determination that the prediction for the at least one condition progress metric computed for the candidate satisfies the at least one screening criteria and determining to not enroll the candidate in the second clinical trial in accordance with a determination that the prediction for the at least one condition progress metric computed for the candidate fails to satisfy the at least one screening criteria.

54. The system of claim 29, wherein screening the candidate comprises determining a role for the candidate in the second clinical trial based on the prediction for the at least one condition progress metric computed for the candidate and the at least one screening criteria.

55. The system of claim 54, wherein determining a role for the candidate comprises determining an analysis grouping in the second clinical trial for the candidate based on the prediction for the at least one condition progress metric computed for the candidate and the at least one screening criteria.

* * * * *